United States Patent
Menkes et al.

(10) Patent No.: US 10,492,473 B2
(45) Date of Patent: Dec. 3, 2019

(54) PET ANIMAL COLLAR FOR HEALTH AND VITAL SIGNS MONITORING, ALERT AND DIAGNOSIS

(71) Applicant: PetPace Ltd., Ramat Hasharon (IL)

(72) Inventors: Avi Menkes, Ramat Hasharon (IL); Asaf Dagan, Ramat Hasharon (IL)

(73) Assignee: PETPACE LTD., Ramat-Hasharon (IL)

( * ) Notice: Subject to any disclaimer, the term of this patent is extended or adjusted under 35 U.S.C. 154(b) by 321 days.

(21) Appl. No.: 15/482,769

(22) Filed: Apr. 9, 2017

(65) Prior Publication Data

US 2017/0208778 A1 Jul. 27, 2017

Related U.S. Application Data

(60) Division of application No. 14/156,526, filed on Jan. 16, 2014, now Pat. No. 9,615,547, which is a
(Continued)

(51) Int. Cl.
*A01K 29/00* (2006.01)
*A01K 27/00* (2006.01)
(Continued)

(52) U.S. Cl.
CPC .......... *A01K 29/005* (2013.01); *A01K 27/001* (2013.01); *A01K 29/00* (2013.01);
(Continued)

(58) Field of Classification Search
CPC .... A01K 27/001; A01K 29/00; A01K 29/005; A01K 15/021; A01K 15/022;
(Continued)

(56) References Cited

U.S. PATENT DOCUMENTS 5,269,312 A 12/1993 Kawamura et al.
5,724,025 A 3/1998 Tavori
(Continued)

FOREIGN PATENT DOCUMENTS

DE 3610960 A1 10/1987
DE 29902099 U1 7/1999
(Continued)

*Primary Examiner* — Thanh Pham
(74) *Attorney, Agent, or Firm* — Mark M. Friedman

(57) ABSTRACT

A system for monitoring vital signs of a pet animal comprises an annular band, an accelerometer configured to measure at least one of resting patterns, activity patterns, movement patterns, position patterns relating to, for example the pet animal relieving itself, lameness and scratching, and a non-accelerometer sensor configured to measure at least one of the following non-accelerometer-measured bioparameters of the pet animal: temperature, pulse rate, respiration rate. One or more processors are configured to receive sensor output data and reference data concerning the measured bioparameters of the pet animal or of a population of the pet animal, and determine a suspicion of a specific medical condition by: (i) scoring at least two bioparameters and comparing a cumulative score to a threshold cumulative score or to a threshold cumulative range; or (ii) identifying an abnormal pattern. The processor(s) may send an alert if at least one specific medical condition is suspected.

20 Claims, 9 Drawing Sheets

Related U.S. Application Data continuation-in-part of application No. 13/400,595, filed on Feb. 21, 2012, now abandoned, and a continuation-in-part of application No. 13/743,383, filed on Jan. 17, 2013, now abandoned.

(60) Provisional application No. 61/507,679, filed on Jul. 14, 2011, provisional application No. 61/522,327, filed on Aug. 11, 2011.

(51) Int. Cl.
| | | |
|---|---|---|
| *A61B 5/00* | (2006.01) | |
| *A61B 5/11* | (2006.01) | |
| *A61D 9/00* | (2006.01) | |
| *A61D 13/00* | (2006.01) | |
| *H04B 1/3827* | (2015.01) | |
| *A61B 5/01* | (2006.01) | |
| *A61B 5/0205* | (2006.01) | |
| *A61B 5/08* | (2006.01) | |
| *A61B 7/00* | (2006.01) | |
| *A61B 5/02* | (2006.01) | |
| *H04B 5/06* | (2006.01) | |

(52) U.S. Cl.
CPC .......... *A61B 5/0004* (2013.01); *A61B 5/0022* (2013.01); *A61B 5/01* (2013.01); *A61B 5/02055* (2013.01); *A61B 5/0816* (2013.01); *A61B 5/1105* (2013.01); *A61B 5/1118* (2013.01); *A61B 5/6822* (2013.01); *A61B 5/6831* (2013.01); *A61B 5/7221* (2013.01); *A61B 5/747* (2013.01); *A61B 7/003* (2013.01); *A61D 9/00* (2013.01); *A61D 13/00* (2013.01); *H04B 1/385* (2013.01); *A61B 5/02* (2013.01); *A61B 5/4094* (2013.01); *A61B 5/6844* (2013.01); *A61B 2503/40* (2013.01); *A61B 2505/07* (2013.01); *A61B 2560/02* (2013.01); *A61B 2562/0219* (2013.01); *A61B 2562/063* (2013.01); *A61B 2562/16* (2013.01); *A61B 2562/164* (2013.01); *H04B 5/06* (2013.01); *H04B 2001/3855* (2013.01)

(58) Field of Classification Search
CPC .... A01K 15/023; A01K 15/029; A01K 15/04; A61D 13/00; A61D 17/00; A61B 2562/00; A61B 2562/02; A61B 2562/14; A61B 2562/16; A61B 5/00; A61B 5/02; A61B 5/0022; A61B 5/0024; A61B 5/11; A61B 5/1105; A61B 5/6822; A61B 5/6844

See application file for complete search history.

(56) References Cited

U.S. PATENT DOCUMENTS

| | | | |
|---|---|---|---|
| 6,283,065 | B1 | 9/2001 | Shorrock et al. |
| 6,661,345 | B1 | 12/2003 | Bevan et al. |
| 6,830,014 | B1 | 12/2004 | Lalor |
| 7,314,450 | B2* | 1/2008 | Iwamiya ............... A61B 5/024 600/481 |
| 7,705,736 | B1 | 4/2010 | Kedziora |
| 2003/0208109 | A1 | 11/2003 | David et al. |
| 2005/0145199 | A1* | 7/2005 | Napolez ............... A01K 15/022 119/718 |
| 2005/0234349 | A1 | 10/2005 | Pravica |
| 2007/0113649 | A1 | 5/2007 | Bharti et al. |
| 2007/0204803 | A1 | 9/2007 | Ramsay |
| 2007/0221140 | A1* | 9/2007 | Warren ............... A01K 11/008 119/859 |
| 2008/0202445 | A1 | 8/2008 | Rugg |
| 2009/0131759 | A1 | 5/2009 | Sims et al. |
| 2009/0149727 | A1* | 6/2009 | Truitt ............... A61B 5/14552 600/323 |
| 2009/0227877 | A1 | 9/2009 | Tran |
| 2009/0227907 | A1* | 9/2009 | Kandori ............... A61B 5/11 600/593 |
| 2010/0010559 | A1 | 1/2010 | Zhang et al. |
| 2010/0063365 | A1* | 3/2010 | Pisani ............... A61B 5/0002 600/301 |
| 2010/0076787 | A1 | 3/2010 | Naylor et al. |
| 2010/0210956 | A1 | 8/2010 | Im |
| 2010/0217533 | A1 | 8/2010 | Nadkarni et al. |
| 2011/0034831 | A1 | 2/2011 | Christensen et al. |
| 2011/0245629 | A1* | 10/2011 | Giftakis ............... A61B 5/0476 600/301 |
| 2012/0006282 | A1 | 1/2012 | Kates |
| 2012/0068848 | A1 | 3/2012 | Campbell et al. |
| 2013/0014706 | A1 | 1/2013 | Menkes |
| 2015/0057963 | A1 | 2/2015 | Zakharov et al. |
| 2015/0164438 | A1* | 6/2015 | Halperin ............... A61B 5/746 340/573.1 |
| 2015/0282768 | A1 | 10/2015 | Luna et al. |
| 2015/0313484 | A1* | 11/2015 | Burg ............... A61B 5/113 600/301 |
| 2015/0373951 | A1* | 12/2015 | Kelly ............... A01K 15/021 119/719 |
| 2016/0302674 | A1 | 10/2016 | Moyer et al. |

FOREIGN PATENT DOCUMENTS

| | | |
|---|---|---|
| FR | 2811217 A1 | 1/2002 |
| JP | 2007195817 A | 8/2007 |
| JP | 2008131862 A | 6/2008 |
| JP | 2008295819 A | 12/2008 |
| WO | 0207644 A2 | 1/2002 |
| WO | 03087737 A1 | 10/2003 |
| WO | 2007100959 A2 | 9/2007 |

* cited by examiner

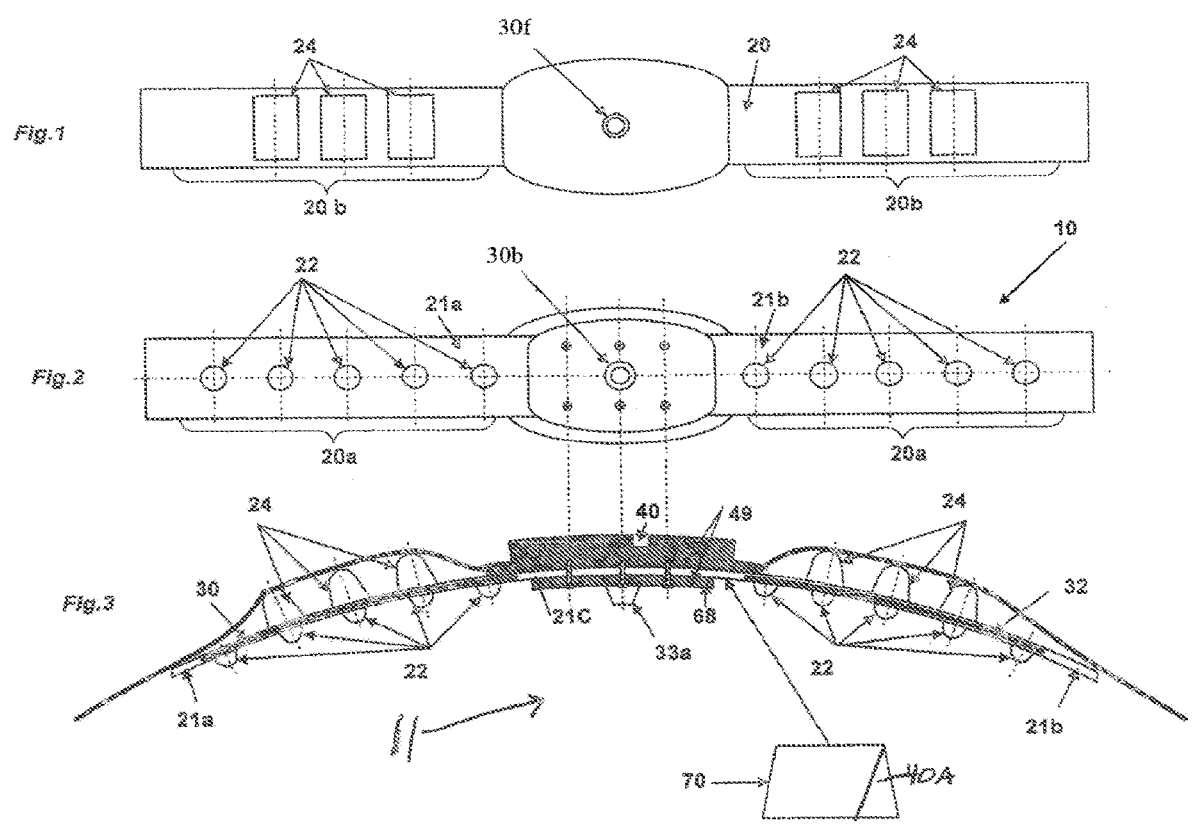

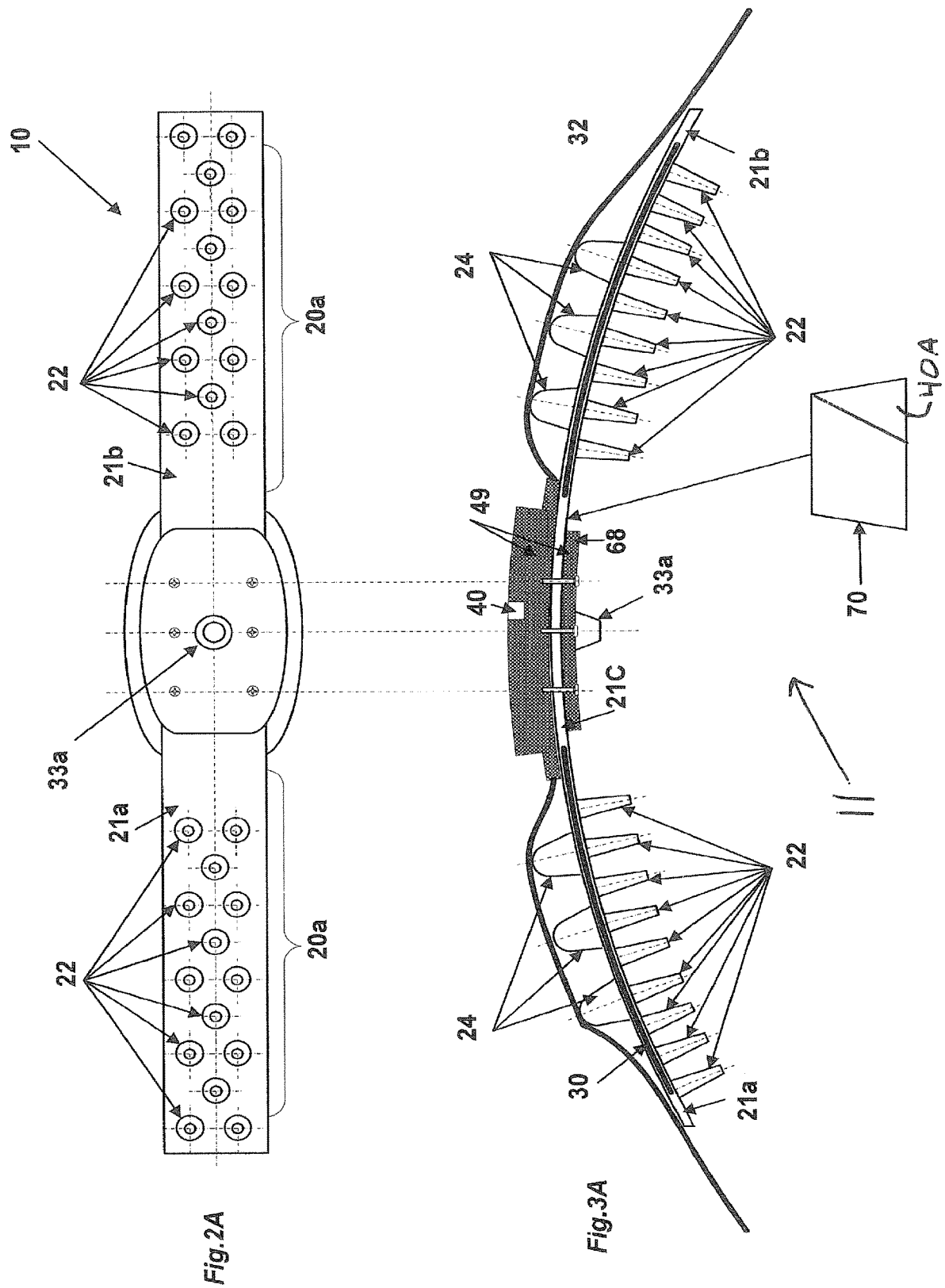

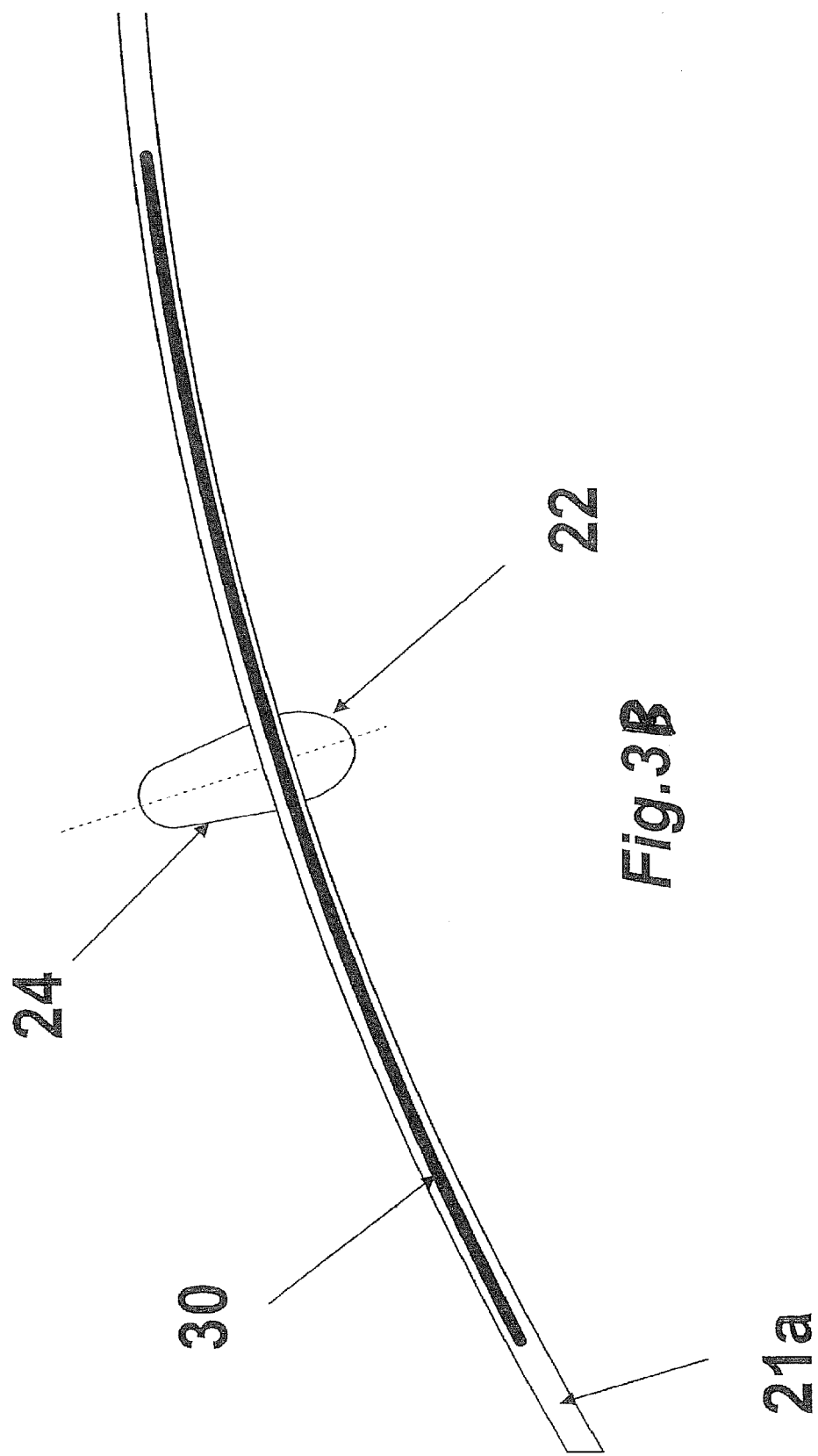

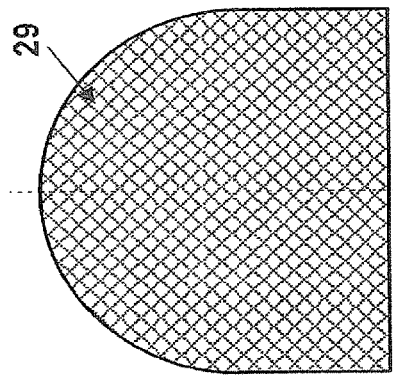
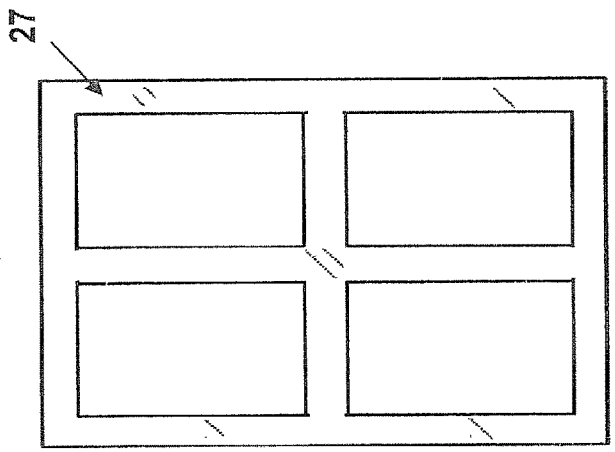
Fig. 7A  Fig. 7B
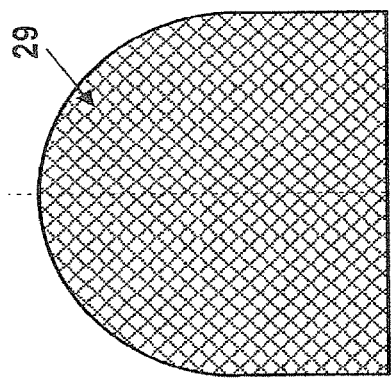
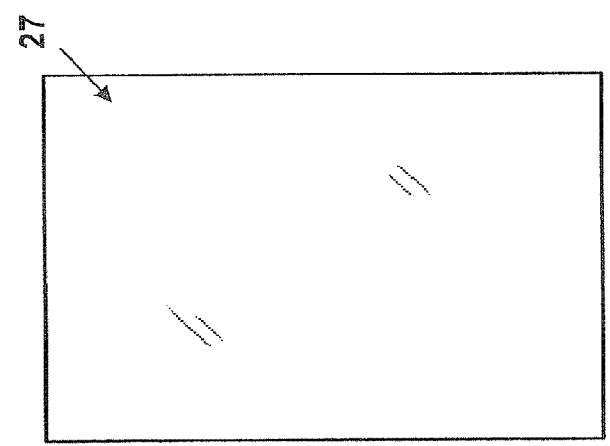
Fig. 8A  Fig. 8B
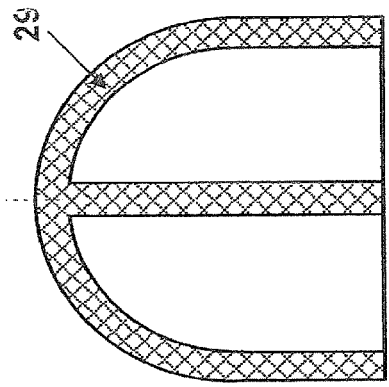
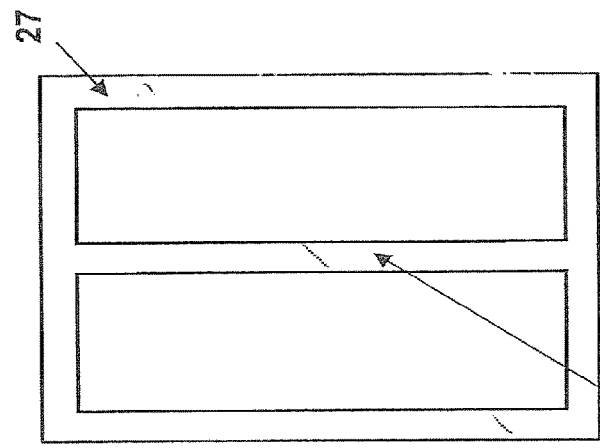
Fig. 9A  Fig. 9B

| METHOD - 100 |

| PROVIDING AN ELASTIC BAND CONFIGURED TO WRAP AROUND A PORTION OF THE PET ANIMAL AND HAVING A WORKING SURFACE AND A REAR SURFACE, AT LEAST ONE SENSOR ELEMENT SITUATED AT ONE OR MORE REGIONS ALONG A CIRCUMFERENCE OF THE BAND AND CONFIGURED TO MEASURE AT LEAST ONE BIOPARAMETER FROM THE FOLLOWING BIOPARAMETERS: TEMPERATURE, HEART RATE, RESPIRATION RATE, MOVEMENT |

↓ 110

| CONFIGURING THE ELASTIC BAND WITH AT LEAST ONE ACOUSTIC CONCENTRATOR PROJECTING FROM THE WORKING SURFACE TOWARD THE PORTION OF THE PET ANIMAL, THE AT LEAST ONE ACOUSTIC CONCENTRATOR SITUATED AT THE ONE OR MORE REGIONS ALONG THE CIRCUMFERENCE AND ON A FIRST SIDE OF THE AT LEAST ONE SENSOR |

↓ 120

| CONFIGURING THE ELASTIC BAND WITH AT LEAST ONE ACOUSTIC BALANCER PROJECTING FROM THE REAR SURFACE AND SITUATED AT THE ONE OR MORE REGIONS ALONG THE CIRCUMFERENCE AND ON A SECOND SIDE OF THE AT LEAST ONE SENSOR ELEMENT, THE AT LEAST ONE LEFT ACOUSTIC BALANCER LOCATED IN A POSITION ALONG THE CIRCUMFERENCE AT LEAST PARTLY BEHIND THE AT LEAST ONE ACOUSTIC CONCENTRATOR |

↓ 130

| TRANSMITTING ELECTRONIC SIGNALS FROM THE SENSOR ELEMENTS TO A PROCESSOR, THE SIGNALS REFLECTING VITAL SIGN MEASUREMENTS OF THE PET ANIMAL |

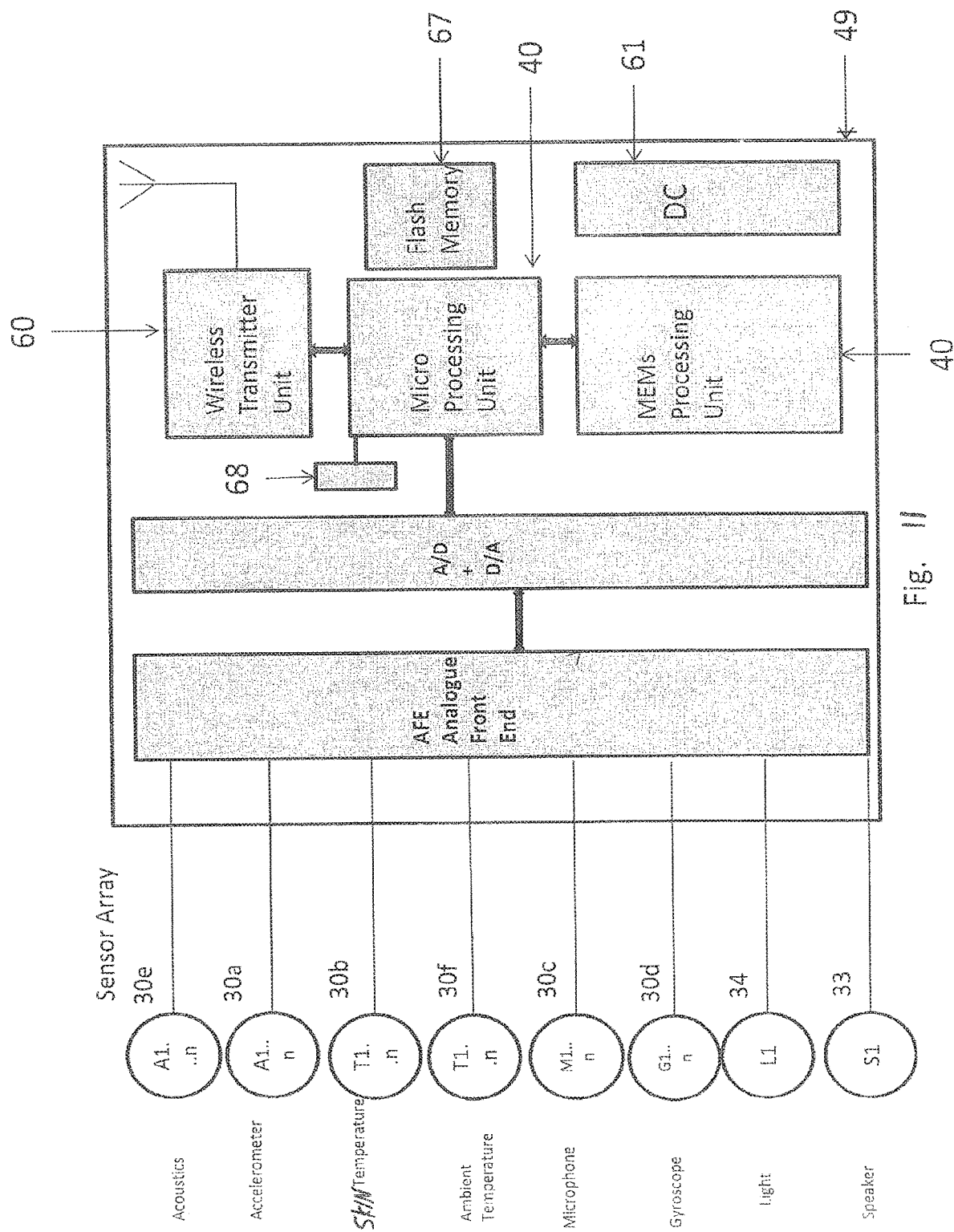

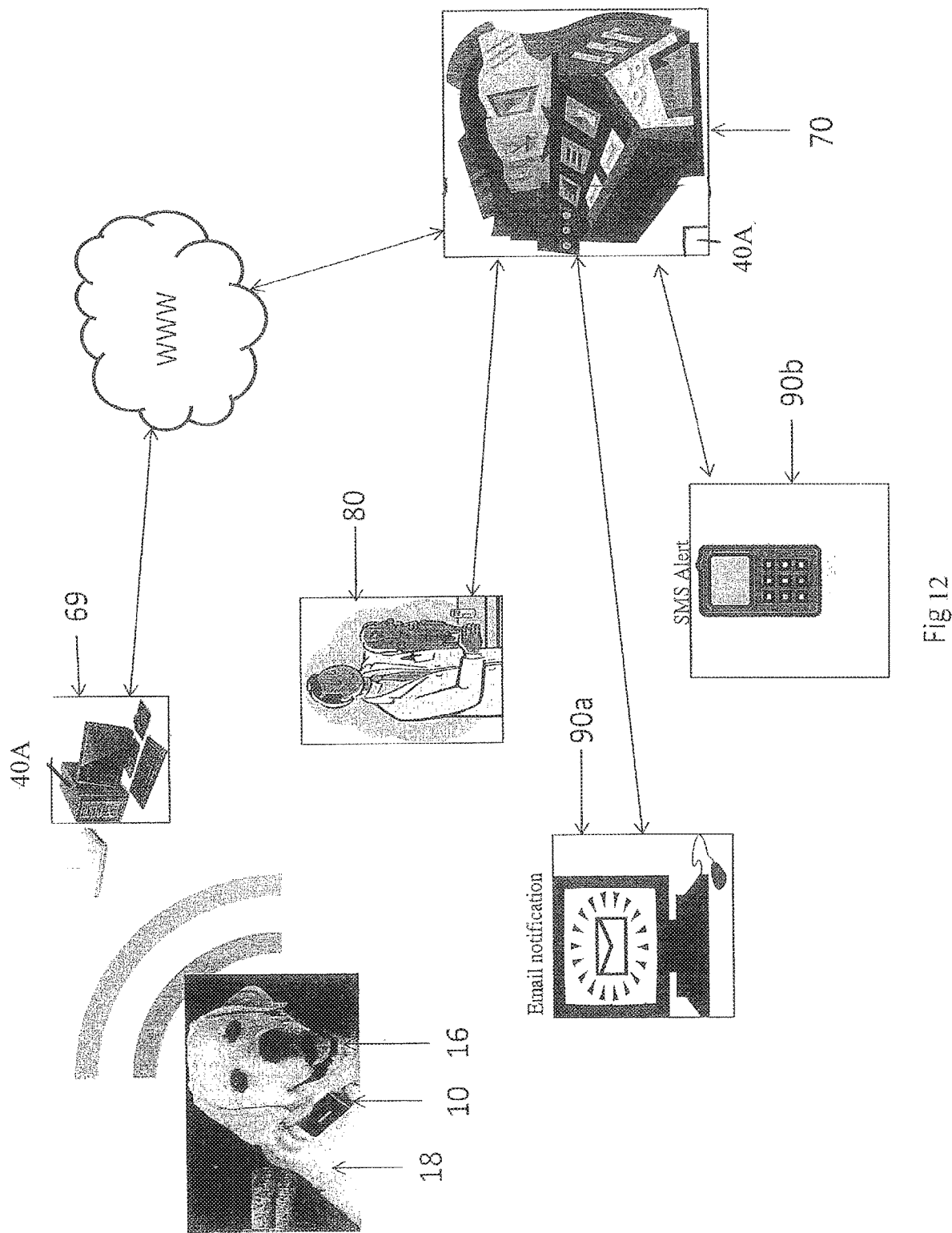

| METHOD - 200 |

PROVIDING AN ANNULAR BAND ON THE PET ANIMAL TO WRAP AROUND A PORTION OF THE PET ANIMAL AND TO HAVE AT LEAST TWO SENSOR ELEMENTS SITUATED AT ONE OR MORE REGIONS ALONG A CIRCUMFERENCE OF THE BAND, THE AT LEAST TWO SENSOR ELEMENTS INCLUDING AN ACCELEROMETER AND A NON-ACCELEROMETER SENSOR, THE ACCELEROMETER CONFIGURED TO MEASURE AT LEAST ONE ACCELEROMETER-MEASURED BIOPARAMETER OF THE PET ANIMAL FROM AMONG: RESTING PATTERNS, ACTIVITY PATTERNS, MOVEMENT PATTERNS, POSITION PATTERNS, LAMENESS AND SCRATCHING, AND THE NON-ACCELEROMETER SENSOR CONFIGURED TO MEASURE AT LEAST ONE OF THE FOLLOWING NON-ACCELEROMETER-MEASURED BIOPARAMETERS OF THE PET ANIMAL: TEMPERATURE, PULSE RATE, RESPIRATION RATE

— 210

ONE OR MORE LOCAL OR REMOTE PROCESSORS RECEIVING (A) SENSOR OUTPUT DATA FROM THE SENSOR ARRAY CONCERNING THE MEASURED BIOPARAMETERS AND (B) REFERENCE DATA CONCERNING THE MEASURED BIOPARAMETERS OF THE PET ANIMAL OR OF A POPULATION OF THE PET ANIMAL, THE ONE OR MORE REMOTE OR LOCAL PROCESSORS CONFIGURED TO DETERMINE WHETHER A SPECIFIC MEDICAL CONDITION IS SUSPECTED BY AT LEAST ONE OF THE FOLLOWING: (I) SCORING AT LEAST TWO BIOPARAMETERS RELATIVE TO THE REFERENCE DATA AND COMPARING A CUMULATIVE SCORE OF ALL SCORED BIOPARAMETERS TO A THRESHOLD CUMULATIVE SCORE OR TO A THRESHOLD CUMULATIVE RANGE; OR (II) IDENTIFYING AN ABNORMAL PATTERN IN AT LEAST ONE BIOPARAMETER FROM AMONG THE ACCELEROMETER-MEASURED BIOPARAMETERS AND THE NON-ACCELEROMETER-MEASURED BIOPARAMETERS

— 220

THE ONE OR MORE REMOTE OR LOCAL PROCESSORS SENDING AN ALERT IF AT LEAST ONE SPECIFIC MEDICAL CONDITION IS SUSPECTED

PET ANIMAL COLLAR FOR HEALTH AND VITAL SIGNS MONITORING, ALERT AND DIAGNOSIS

PRIORITY INFORMATION

This nonprovisional U.S. patent application claims the benefit of and priority to and is a continuation in part patent application of Applicant's U.S. patent application Ser. No. 13/400,595 filed Feb. 21, 2012 and Ser. No. 13/743,383 filed Jan. 17, 2013, both of which are pending.

FIELD AND BACKGROUND OF THE INVENTION

The present invention relates to apparatuses and methods for monitoring vital signs and health of animals, and, more particularly for monitoring the health and vital signs of pet animals, such as dogs and cats, and doing so using a specially designed collar.

When animals, including pets such as dogs and cats, are sick they tend by nature to withdraw and hide since they feel defenseless. This behavior makes detection of diseases and treatment of the animal significantly more difficult. With regard to pet animals, such as dogs and cats, it is standard medical practice to check the vital signs of a sick dog or a sick cat. However, this tends to occur long after the animal has contracted the medical problem either because the dog or cat was concealing its symptoms and/or because it takes time to reach the veterinarian. Early detection is often not achieved yet is very important in order to achieve less suffering of the pet and less likelihood of a severe disease, which can develop if detection occurs late. Regarding ear infections in a dog, for example, according to Veterinary Pet Insurance (VPI), this is the most common medical condition affecting dogs in 2010 and "identifying changes or redness early will help dogs and cats avoid more irritating, painful and expensive ear infections. The longer a problem is allowed to persist, the more difficult it is to treat."

Moreover, dogs and cats whose owners are not constantly with them as a practical matter, and dogs and cats whose owners are medically trained, are more vulnerable to contracting an illness, exhibiting symptoms-hiding behavior patterns and decreasing the chances of timely medical intervention.

In addition, monitoring the health of captive animals, for example animals in zoos, is an arduous and expensive task.

There is a compelling need to have an apparatus and method that will provide early detection and diagnosis of pet animals such as dogs and cats, and to do so accurately and efficiently without interfering with the comfort and behavior of the animal.

SUMMARY OF THE PRESENT INVENTION

One aspect of the present invention is a system for monitoring vital signs of a pet animal, comprising an annular band having a working surface configured to wrap around a portion of a pet animal; a sensor array comprising at least two sensor elements situated along a circumference of the band, the at least two sensor elements including an accelerometer and a non-accelerometer sensor, the accelerometer configured to measure at least one accelerometer-measured bioparameter of the pet animal from among: resting patterns, activity patterns, movement patterns, position patterns, lameness and scratching, and the non-accelerometer sensor configured to measure at least one of the following non-accelerometer-measured bioparameters of the pet animal: temperature, pulse rate, respiration rate; one or more remote or local processors configured to receive (a) sensor output data from the sensor array concerning the measured bioparameters and (b) reference data concerning the measured bioparameters of the pet animal or of a population of the pet animal, the one or more remote or local processors configured to determine whether a specific medical condition is suspected by at least one of the following: (i) scoring at least two bioparameters relative to the reference data and comparing a cumulative score of all scored bioparameters to a threshold cumulative score or to a threshold cumulative range; or (ii) identifying an abnormal pattern in at least one bioparameter from among the accelerometer-measured bioparameters and the non-accelerometer-measured bioparameters, the one or more remote or local processors configured to send an alert if at least one specific medical condition is suspected.

A further aspect of the present invention is a system for monitoring vital signs of a pet animal, comprising an annular band having a working surface configured to wrap around a portion of a pet animal; one or more accelerometers situated along a circumference of the band and configured to measure at least one bioparameter of the pet animal from among: resting patterns, activity patterns, movement patterns, position patterns, lameness and scratching, one or more remote or local processors configured to receive (a) sensor output data from the one or more accelerometers concerning the measured bioparameters and (b) reference data concerning the measured bioparameters of the pet animal or of a population of the pet animal, the one or more remote or local processors configured to determine whether a specific medical condition is suspected by at least one of the following: (i) scoring at least two bioparameters and comparing a cumulative score of all scored bioparameters to a threshold cumulative score or to a threshold cumulative range; or (ii) identifying an abnormal pattern in at least one accelerometer-measured bioparameter, the one or more remote or local processors configured to send an alert if at least one specific medical condition is suspected.

A still further aspect of the present invention is a method of monitoring pet animals to determine a suspicion of a specific medical condition in the pet animals, comprising providing an annular band on the pet animal to wrap around a portion of the pet animal and to have at least two sensor elements situated at one or more regions along a circumference of the band, the at least two sensor elements including an accelerometer and a non-accelerometer sensor, the accelerometer configured to measure at least one accelerometer-measured bioparameter of the pet animal from among: resting patterns, activity patterns, movement patterns, position patterns, lameness and scratching, and the non-accelerometer sensor configured to measure at least one of the following non-accelerometer-measured bioparameters of the pet animal: temperature, pulse rate, respiration rate; one or more local or remote processors receiving (a) sensor output data from the sensor array concerning the measured bioparameters and (b) reference data concerning the measured bioparameters of the pet animal or of a population of the pet animal, the one or more remote or local processors configured to determine whether a specific medical condition is suspected by at least one of the following: (i) scoring at least two bioparameters relative to the reference data and comparing a cumulative score of all scored bioparameters to a threshold cumulative score or to a threshold cumulative range; or (ii) identifying an abnormal pattern in at least one bioparameter from among the accelerometer-measured bioparameters and the non-accelerometer-measured bioparameters; and the one or more remote or local processors sending an alert if at least one specific medical condition is suspected.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 1 is a top view of an opened collar, in accordance with one embodiment of the present invention;

FIG. 2 is a bottom view of the collar of FIG. 1, in accordance with one embodiment of the present invention;

FIG. 2A is a bottom view similar to FIG. 2 but having differently shaped acoustic concentrators, in accordance with one embodiment of the present invention;

FIG. 3 is a longitudinal sectional view of an opened collar, in accordance with one embodiment of the present invention;

FIG. 3A is a longitudinal sectional view of an opened collar of FIG. 2A, in accordance with one embodiment of the present invention;

FIG. 3B is an enlarged sectional view of a portion along the circumference of the collar showing a piezoelectric element inside the band, in accordance with one embodiment of the present invention;

FIG. 7A is a vertical sectional view of a cross-shaped acoustic balancer, in accordance with one embodiment of the present invention;

FIG. 7B is a bottom view of the acoustic balancer of FIG. 7A, in accordance with one embodiment of the present invention;

FIG. 8A is a vertical sectional view of a solid acoustic balancer, in accordance with one embodiment of the present invention;

FIG. 8B is a bottom view of the acoustic balancer of FIG. 8A, in accordance with one embodiment of the present invention;

FIG. 9A is a vertical sectional view of a dot shaped acoustic balancer, in accordance with one embodiment of the present invention;

FIG. 9B is a bottom view of the acoustic balancer of FIG. 9A, in accordance with one embodiment of the present invention; and FIG. 10 is a flow chart showing a method, in accordance with one embodiment of the present invention.

FIG. 11 is a high level scheme of a sensor array and associated electronics, the electronics inside a controller, in accordance with one embodiment of the present invention;

FIG. 12 is a schematic of the architecture of an overall system, in accordance with one embodiment of the present invention; and FIG. 13 is a flow chart showing a method, in accordance with one embodiment of the present invention.

DETAILED DESCRIPTION OF THE INVENTION

Figures 6A, 6B:
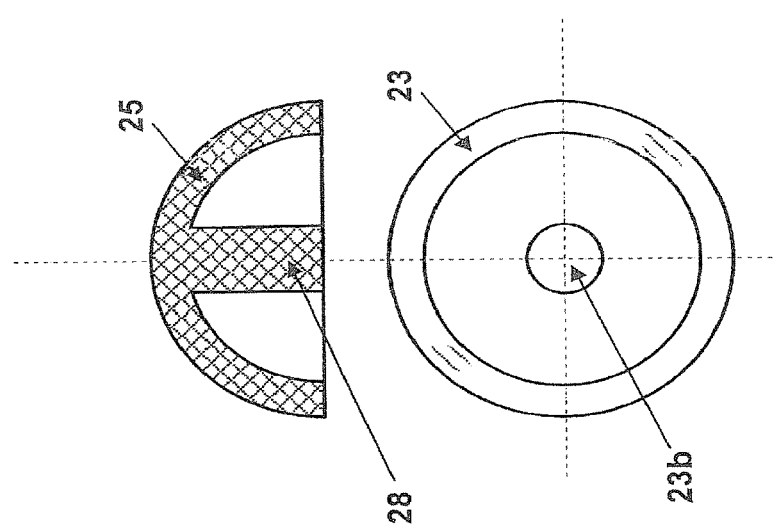
FIG. 6A is a vertical sectional view of a dot shaped acoustic concentrator, in accordance with one embodiment of the present invention.
FIG. 6B is a bottom view of the acoustic concentrator of FIG. 6A, in accordance with one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides a system for monitoring vital signs of pet animals such as dogs and cats and determining a suspicion of a specific medical condition. An annular band may have a working surface configured to wrap around a portion of a pet animal. A sensor array may comprise at least two sensor elements situated along a circumference of the band, the at least two sensor elements including an accelerometer and a non-accelerometer sensor, the accelerometer configured to measure at least one accelerometer-measured bioparameter of the pet animal from among: resting patterns, activity patterns, movement patterns, position patterns (for example relating to the pet animal relieving itself), lameness and, scratching (and others in some preferred embodiments), and the non-accelerometer sensor configured to measure at least one of the following non-accelerometer-measured bioparameters of the pet animal: temperature, pulse rate, respiration rate. One or more remote or local processors may be configured to receive (a) sensor output data from the sensor array concerning the measured bioparameters and (b) reference data concerning the measured bioparameters of the pet animal or of a population of the pet animal, the one or more remote or local processors configured to determine whether a specific medical condition is suspected by at least one of the following: (i) scoring at least two bioparameters relative to the reference data and comparing a cumulative score of all scored bioparameters to a threshold cumulative score or to a threshold cumulative range; or (ii) identifying an abnormal pattern in at least one bioparameter from among the accelerometer-measured bioparameters and the non-accelerometer-measured bioparameters. The one or more remote or local processors configured to send an alert if at least one specific medical condition is suspected.

The annular band may comprise a layer of an elastic material. The annular band may be configured to measure at least one bioparameter from the following bioparameters: temperature, heart rate, respiration rate, movement and positions. At least one acoustic concentrator, in the form of a bump, may project toward the neck or other body portion of the pet animal from the working surface at the one or more regions along the circumference. In addition, at least one acoustic balancer may project from the rear surface at the one or more regions along the circumference. The at least one acoustic balancer may be situated at a region along the circumference at least partly behind and preferably directly behind the at least one acoustic concentrators. Each of the acoustic concentrators may be wider at a concentrator base end adjacent the working surface than at a concentrator top end and likewise each of the acoustic balancers may be wider at a balancer base end adjacent the rear surface than at a balancer top end. In one preferred embodiment, the acoustic concentrators and preferably also the balancers have a circular cross-section due to a conical shape of the acoustic concentrators (see FIG. 3A). In another preferred embodiment, the acoustic concentrators, and preferably also the balancers have an X-shaped cross-section.

The collar may have sensor elements that can be activated remotely to check vital signs of the animal (such as respiration, pulse, temperature, movement and positions) and a processor that can interpret the results of multiple vital sign readings. The collar may also have a two way communication device attached or integrated thereto that can alert the pet owner, a veterinarian or the authorities, when appropriate, that a pet animal is suffering from a particular condition or is exhibiting suspicious behavior or movements. This way, a veterinarian can remotely take a particular vital sign measurement when alerted of the data by signalling the processor to actuate a particular sensor element. The sensor elements that may be embedded in the band of the collar may gather data that can be processed on the collar itself or transmitted to a remote terminal, which can be a home computer, a hand-held device, or a main server computer. In order to dramatically improve the system gain, sensitivity and signal to noise ratio (SNR), an elastic layer may absorb noise from friction due to movement of the animal's head.

In contrast to prior art pet animal collars, which do not measure vital signs, the pet collar of the present invention may measure vital signs of the pet animal. For example, it may measure, heart rate, respiration rate, temperature, movement, body positions etc. In contrast to the prior art monitoring systems that may utilize multiple sensors, which may generate many alerts over a short period of time, sometimes even simultaneously, a situation that may overload the system, increase its cost or limit its applicability, the system and method of the present invention may avoid these drawbacks not just by sensing a large number of bioparameters of the pet animal, but also by fusing the sensed data together. As an example, although twitching by a dog may exemplify an abnormal pattern of movement consistent with a seizure, generating an alert based on this may often result in a false positive alert. Instead, the system of the present invention may combine that data with data sensed concerning the position of the dog, for example whether the dog is lying down. This may greatly decrease the risk that a false alarm for seizure will be generated. In further contrast to prior art monitoring systems, in which alerts may be produced unreliably if the pet animal is in a specific environment, or in a certain state or context that may mask a healthy condition, the system and method of the present invention may combine certain sensor data with data identifying the specific environment or state of the pet animal, thereby avoiding a false alarm. For example, if the multiple sensors merely detect bioparameters including pulse rate, then a false alarm for a particular medical condition like acute or chronic pain may result, whereas the system of the present invention may combine that pulse rate data with movement and position data identifying whether the animal is excited or playing, which could explain the increased pulse rate without illness. Likewise, other states, environments or contexts such as exercising in hot weather could create a false alarm for a medical condition whose suspected diagnosis is grounded in part on increased temperature. Similarly, sleeping could create a false alarm for a medical condition whose suspected diagnosis is grounded in part on low pulse rate. Accordingly, the one or more processors of the system of the present invention may combine the pulse rate and other sensor data together with data identifying the state or environment of the pet animal, in order to reach a much more reliable determination as to whether the particular medical condition is suspected and thereby reduce the chance of a false suspected diagnosis and alarm. In still further contrast to prior art monitoring systems, the system of the present invention may include one or more remote and local processors. For example, a local processor on a collar may relay data to a remote processor in a server computer located in cyberspace. The system of the present invention, in contrast to the prior art, may interpret the interdependence of the vital sign measurements made by the sensor array to arrive at a suspicion of a medical diagnosis that may be relayed to a veterinarian, the pet owner and/or to the authorities. In still further contrast to the prior art, the collar may have two-way communication so that a veterinarian can instruct the collar to measure a particular vital sign remotely. In still further contrast to the prior art animal pet collars, such as dog collars, in which signal to noise ratio precludes remote telecommunication reception of vital sign parameters, the collar of the present invention may include a layer of elastic that improves the signal to noise ratio by absorbing friction from constant movement of the dog or pet's head. In contrast to the prior art collars, the collar of the present invention may also have a GPS and communications system for alerting remote personnel so that if the pet animal is out of a designated area, or if a captive animal in a zoo escapes its enclosure, an immediate alarm can be sounded and an alert transmitted to designated authorities and veterinarians. In further contrast to prior art methods and apparatuses of monitoring the pet animals' vital signs, which may interfere with the pet animal's behavior or cause irritation, for example because the collar has to be too tight, or which may not be sufficiently effective in capturing the low frequency sounds made by the animal, due to the fur of the animal around the neck of the animal, the collar and method of the present invention may provide an effective method of monitoring the vital signs and diagnosing the health condition of the pet animal accurately without adversely affecting the behavior or comfort of the animal. Despite its accuracy, the collar may only need to gently touch the animal's neck, for example through its fur, at several points around the neck. In still further contrast to the prior art animal pet collars, such as dog collars, in which signal to noise ratio precludes remote telecommunication reception of vital sign parameters, the collar of the present invention may include a layer of elastic material that may improve the sensitivity, gain and signal to noise ratio by absorbing friction from constant movement of the dog or pet's head. In still further contrast to the prior art collars, which may not be accurate in capturing the low frequency sounds made by the animal, the collar and method of the present invention may utilize an acoustically enhanced collar whose band for positioning on a neck of the pet animal may have a working surface and a rear surface, at least one and preferably at least two acoustic concentrators projecting toward a neck of the pet animal from the working surface on one side of the at least one sensor element and at least one and preferably at least two acoustic balancers projecting from the rear surface on the other side of the at least one sensor. An acoustic balancer may be positioned at least partly behind a corresponding acoustic concentrator, and in some preferred embodiments the positioning maybe such that most or all of the acoustic concentrators have an acoustic balancer at least partly behind it on opposite sides of the band. In further contrast to prior art collars, in which the structure of the device does not optimize capturing the low frequency sound by creating a balanced acoustic signal that is readable and able to be parsed, the collar of the present invention may have enhanced ability to convert low mechanical pulses to electrical signals of reasonable magnitude for transmission to the processor and thereby capture the low frequency sound effectively as a balanced acoustic signal that is readable and able to be parsed. Furthermore, in contrast to the prior art, the acoustic enhancers (concentrators and balancers) of the collar of the present invention may perform this function while simultaneously reducing total noise by reducing relative movement between the collar and the pet animal's head when the pet animal's head moves. The acoustic concentrators in the form of bumps may prevent occasional rotation of the collar relative to the neck of the animal. Instead, the collar of the present invention may move with the animal's head when the animal turns its head due to the inward facing acoustic concentrators. Keeping the collar at the desired place may be critical both for the accuracy of the acoustic sensor and for the accuracy of the acceleration/position sensor that may be on the collar. As a result of the acoustic concentrators and acoustic balancers in a preferred embodiment of the system 11 of the present invention, the signal to noise ratio expressed using the logarithmic decibel scale may be at least 20 dB and in some preferred embodiments between 20 dB and 40 dB. The typical pulse amplitude is between 300 and 500 mV, as defined by the gain setting of the amplifier (not shown). By having a better signal to noise ratio, in contrast of the prior art, the system of the present invention may be better able to provide reliable data that passes a quality assurance test, and hence may be able to provide a reliable suspicion of a medical condition with fewer sensors.

The principles and operation of a system, apparatus and method for a pet animal collar for health & vital signs monitoring, alert and diagnosis may be better understood with reference to the drawings and the accompanying description.

As seen from FIGS. 1-13, especially FIGS. 1-3B, a preferred embodiment of a system of the present invention may be a system 11 for monitoring vital signs of a pet animal. System 11 may comprise an annular band 20, which may be in the form of a collar 10. Annular band 20 may have a working surface 20a configured to wrap around a portion of a pet animal. The annular band may comprise a layer of an elastic material. Band 20 may also have a rear surface 20b facing an opposite direction to the working surface 20a.

In one preferred embodiment, system 11 may include a sensor array comprising at least two sensor elements situated along a circumference of the band 20, the at least two sensor elements including an accelerometer and a non-accelerometer sensor, the accelerometer configured to measure at least one accelerometer-measured bioparameter of the pet animal from among: resting patterns, activity patterns, movement patterns, position patterns such as relating to the pet animal relieving itself, lameness and scratching, and the non-accelerometer sensor configured to measure at least one of the following non-accelerometer-measured bioparameters of the pet animal: temperature, pulse rate, respiration rate. The at least two sensor elements may comprise at least three or at least four or at least five or at least six or at least seven (or more) sensor elements distributed at different points along the circumference of the band.

System 11 may also comprise one or more remote (40A) or local processors 40 configured to receive (a) sensor output data from the sensor array concerning the measured bioparameters and (b) reference data concerning the measured bioparameters of the pet animal or of a population of the pet animal.

The one or more remote or local processors may include one or more local processors 40 and/or one or more remote processor 40A.

The one or more local or remote processors 40, 40A may be configured to determine whether a specific medical condition is suspected by utilizing at least one of the following: (i) scoring at least two bioparameters relative to the reference data and comparing a cumulative score of all scored bioparameters to a threshold cumulative score or to a threshold cumulative range; or (ii) identifying an abnormal pattern in at least one bioparameter from among the accelerometer-measured bioparameters and the non-accelerometer-measured bioparameters. The one or more remote or local processors may be configured to send an alert if at least one specific medical condition is suspected. Accordingly, as seen in FIG. 12, in some preferred embodiments of the system of the present invention, the system may further comprise a two-way communication device, which may be attached to annular band 20, for communicating the suspicion in a form of an alert to a remotely stationed veterinarian or other user.

Note that if the one or more local or remote processors of system 11 consist solely of local processors 40 (i.e. processors situated in or on or at collar 10), then the system 11 can also be described as an apparatus or device 10, which apparatus or device may be described as a collar 10 having various components. On the other hand, if the system 11 includes at least one remote processor 40A, or even one remote device such as a communication device, the system 11 is not an apparatus but includes an apparatus such as a collar 10.

In system 11, the one or more processors 40, 40A may be configured to combine the identifying of the abnormal pattern in the at least one bioparameter with identifying abnormal patterns in at least one other bioparameter. For example, the identifying of the abnormal pattern in the at least one bioparameter involves identifying said abnormal patterns in at least one accelerometer-measured bioparameter and identifying abnormal patterns in at least one non-accelerometer-measured bioparameter.

If, for example, the specific medical condition is seizure and the abnormal pattern in the at least one accelerometer-measured bioparameters is an abnormal pattern of movement comprising at least one of paddling, head shaking or twitching occurring when the pet animal is lying down on either side, the abnormal pattern of movement sensed by the accelerometer.

In preferred embodiments, the sensor output data from the sensor array concerning the bioparameters may be test to see if it passes a quality assurance test. The quality assurance test may be based on a threshold level of signal to noise ratio. Accordingly, the at least one acoustic concentrator and at least one balancer that are utilized in a preferred embodiment may greatly improve the signal to noise ratio and allow the data to pass the quality assurance test. In certain other preferred embodiments, the quality assurance test may be based on a pattern recognition. In still other preferred embodiments, the bioparameters are to see if they pass a quality assurance test, wherein the quality assurance test is based on whether a quantity of data points of the data is sufficiently high.

The following is an example of certain logic used in combining data from different sensors (data fusion) by the one or more local or remote processors in accordance with certain preferred embodiments. For the medical condition of seizures/convulsions, an accelerometer senses activity data ("A") for example by detecting patterns of movement suspicious of seizures (paddling, head shaking, twitching). This detection is considered a necessary component for detecting this condition in accordance with this preferred embodiment. The accelerometer also senses position data ("B") to confirm that the activity data pattern must happen while the pet is lying down (on either side). According to this logic, Activity+Position (A+B) parameters are necessary components. (A+B) parameters may even be considered as sufficient components, if the data relating to them is considered of good enough quality (high confidence), i.e., if the incoming data receives a passing score when subjected to one or more quality assurance tests.

If, on the other hand, the activity and position incoming data (A+B) is merely of medium quality or of borderline confidence, and hence inconclusive, then supplemental data from the following other sensors that may sense other parameters may support a suspicion of seizures. The supplemental data may be pulse data that shows an increased pulse rate at rest. This is a strong supportive component for a suspicion of seizures/convulsions. The supplemental data may be respiration data that shows increased respiration rate at rest—this is a supportive component for a suspicion of seizures/convulsions. The supplemental data may be data concerning sounds from an acoustic accelerometer, i.e. whining, yelping. This is a supportive component for a suspicion of seizures/convulsions. In sum, in this preferred embodiment, A+B at a level of good score on a quality assurance test would yield an alert. Furthermore, A+B at a level of a medium score on a quality assurance test plus one or more supplemental data would yield an alert.

In one preferred embodiment, for the medical condition of GDV, each parameter and basic/background attributes may be assigned a pre-determined score. No one parameter is necessary but rather a sufficient accumulation of supporting parameters. The scores of all parameters are summed and if at any time the cumulative score passes a threshold score, then an alert is generated. For the medical condition of hyperthyroidism, the logic may be the same logic as GDV, but the difference is that since this is a chronic disease, slowly progressing, the scoring will also depend on persistence of the abnormal parameters over time.

Accordingly, in one preferred embodiment, the one or more remote or local processors may be configured to determine a suspicion of seizure based also on at least one of sound, pulse and respiration, wherein pulse means pulse rate or pulse rhythm.

In general, the one or more local or remote processors may be configured to determine whether each of the at least two bioparameters exceeds a threshold level or range. Alternatively, the one or more remote or local processors may be configured to determine whether a new parameter that is a function of a combination of each of the at least two relevant bioparameters, and may be configured to determine if the new parameter exceeds a threshold level or range.

In general, in order to combine data received from sensor to include information about environments or states of the pet animal, the sensor array may be configured to measure at least one of the following characteristics of the pet animal for output to the one or more remote or local processors: sleeping/resting patterns, eating/drinking patterns, position patterns relating to the animal relieving itself and existence of stress or pain.

For example, for the specific medical condition of gastric dilation-volvulus (GDV), the one or more remote or local processors are configured to base a suspicion of GDV at least in part on scoring at least two bioparameters from among (i) restlessness including reluctance to lie down or pacing, (ii) vomiting sounds (iii) sounds indicative of not eating, (iv) sounds indicative of grunting or groaning, (v) sounds indicative of pain, (vi) increased respiration rate and respiration effort, (vii) increased pulse rate (viii) irregular pulse rhythm (ix) loss of sinus arrhythmia, and (x) a pattern of ingestion of a large meal followed by exercise followed by attempts to vomit, and comparing a cumulative score of all scored bioparameters to a threshold cumulative score or to a threshold cumulative range.

Likewise, for the specific medical condition of hyperthyroidism, the one or more remote or local processors are configured to base a suspicion of hyperthyroidism at least in part on scoring at least two bioparameters from among (i) increased activity level, (ii) vomiting sounds (iii) sounds indicative of not eating, (iv) sounds indicative of vomiting or diarrhea, (v) increased pulse rate or irregular pulse rate, (vi) increased respiration rate, (vii) increased number of visits to a litter box (viii) increased frequency or time spent of drinking as measured by acoustic accelerometer, (ix) increased frequency and time spent eating as measured by proximity sensors, comparing a cumulative score of all scored bioparameters to a threshold cumulative score or to a threshold cumulative range; and measuring a persistence over time of either the cumulative score or the abnormal pattern.

If the accelerometer is an acoustic accelerometer configured to measure sounds, it may be configured to measure a presence of at least one or at least two pet animal sounds, or in other preferred embodiments, at least three pet animal sounds, or at least four pet animals sounds (or in other preferred embodiments at least five or at least six or seven or eight or at least nine or ten or eleven) among yelping, whining, wheezing, hissing, purring, stridor, stertor, coughing, barking, growling and grunting.

If the pet animal is a dog, the system may be configured to determine a suspicion of at least one or at least two or at least three, or at least four, or at least five, or at least six, or at least seven, or at least eight, or at least nine, or at least ten, of the following specific medical conditions of dogs: skin allergies, ear infection, skin infection, upset stomach/vomiting, arthritis, lameness, intestinal upset/diarrhea, bladder infection, periodontitis/dental disease, obesity and pain. If the pet animal is a cat, the system may be configured to determine a suspicion of at least one or at least two or at least three, or at least four, or at least five, or at least six, or at least seven, or at least eight, or at least nine, or at least ten, of the following specific medical condition: bladder infection, periodontitis/dental disease, overactive thyroid, chronic kidney disease, upset stomach/vomiting, diabetes, intestinal upset/diarrhea, skin allergies, lymphosarcoma, and upper respiratory infection.

In certain preferred embodiment of the system of the present invention, instead of both accelerometers and other sensors, the sensors of system 11 may be limited to one or more accelerometers situated along a circumference of the band. The one or more accelerometers may include acoustic accelerometers and non-acoustic accelerometers. The one or more accelerometers may be configured to measure at least one bioparameter of the pet animal from among: resting patterns, activity patterns, movement patterns, position patterns relating to, for example, the pet animal relieving itself, lameness and scratching. If the sensors are limited to one or more accelerometers, the one or more remote or local processors may be configured to receive (a) sensor output data from the one or more accelerometers concerning the measured bioparameters and (b) reference data concerning the measured bioparameters of the pet animal or of a population of the pet animal, the one or more remote or local processors configured to determine whether a specific medical condition is suspected by at least one of the following: (i) scoring at least two bioparameters and comparing a cumulative score of all scored bioparameters to a threshold cumulative score or to a threshold cumulative range; or (ii) identifying an abnormal pattern in at least one accelerometer-measured bioparameter.

As seen from FIGS. 1-3B, one version of the system or method of the present invention may utilize an acoustically enhanced collar 10 for monitoring vital signs of a pet animal. For example, a collar 10 may include a band 20 that may comprise a layer of an elastic material, for example polyurethane. The elastic material may include any kind of plastic or other flexible material, although in a preferred embodiment, elastic material may comprise polyurethane. The band 20 may be configured for cushioning repetitive instances of friction against the collar 10 from movement of the head of the pet animal. Although the remainder of this application may refer primarily to the "neck" of the pet animal, it should be understood that other portions of the animal may also hold the collar.

As seen from FIGS. 1-3B, band 20 may have a working surface 20a that may be configured to wrap around a portion of a pet animal, for example a neck 16 (see FIG. 12) of the animal 18 (see FIG. 12) which may be a dog, and may have a rear surface 20b that may face an opposite direction from working surface 20a. For example, working surface 20a may face the animal's neck and rear surface 20b may face a viewer looking directly at the band 20 of the collar 10 on the neck of the animal. Band 20 (and collar 10) may be approximately two inches wide and may cover an entire circumference of the neck of the pet (or alternatively most or a portion of this circumference). There may be sensors 30, for example four or more sensor elements 30 at different points of the band, preferably at different points along a length or circumference of band 20. There may be other numbers of sensor elements, such as one, two, three, five, six, seven, eight, nine or ten and more.

As seen from FIGS. 1-3B, the annular band may have at least one acoustic concentrator projecting toward a body portion of the pet animal from the working surface at one or more regions along the circumference; and may have at least one acoustic balancer projecting from the rear surface at the one or more regions along the circumference. The at least one acoustic balancer may be situated at a region along the circumference at least partly behind the at least one acoustic concentrators.

Figures 5A, 5B:
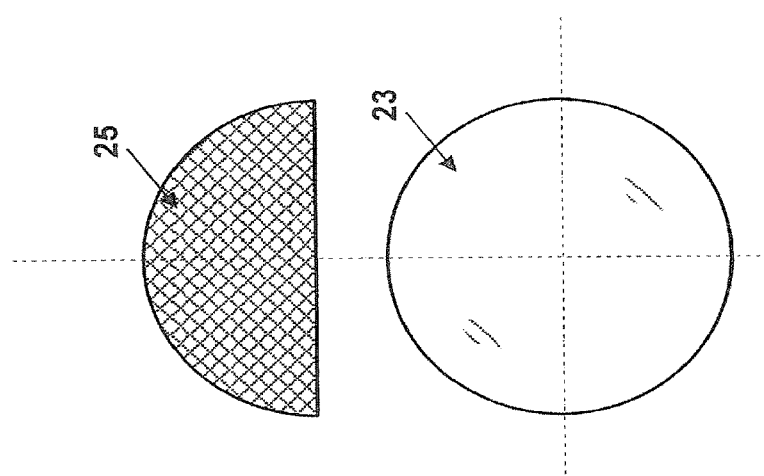
FIG. 5A is a vertical sectional view of a solid acoustic concentrator, in accordance with one embodiment of the present invention.
FIG. 5B is a bottom view of the acoustic concentrator of FIG. 5A, in accordance with one embodiment of the present invention.
Figures 4A, 4B:
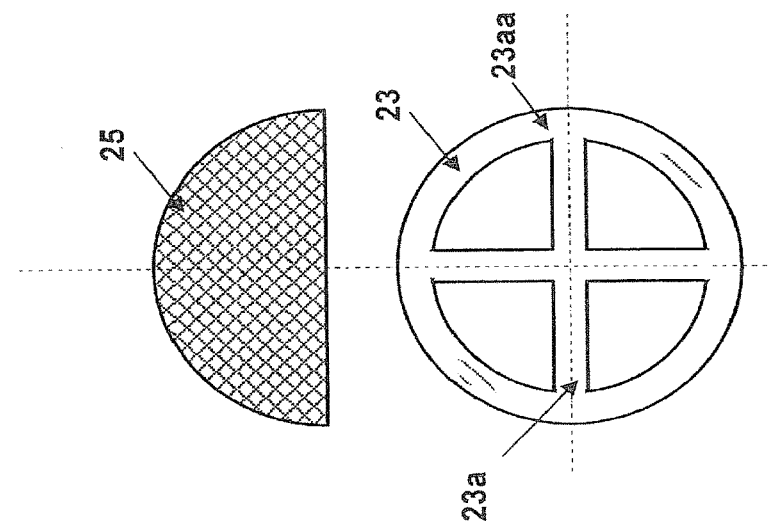
FIG. 4A is a vertical sectional view of a cross-shaped acoustic concentrator, in accordance with one embodiment of the present invention.
FIG. 4B is a bottom view of the acoustic concentrator of FIG. 4A, in accordance with one embodiment of the present invention.

Each acoustic concentrator 22 may have a concentrator base end 23, which refers to the base of the acoustic concentrator adjacent the working surface 20a, (see FIGS. 4B, 5B, 6B). Each acoustic concentrator 22 may have a concentrator top end 25 (see FIGS. 4A, 5A, 6A), the end projecting furthest from the band 20 and closest to the animal's neck, for example. Likewise, each acoustic balancer 24 may have a balancer base end 27 (see FIGS. 7B, 8B, 9B) and a balancer top end 29 (see FIGS. 7A, 8A, 9A).

In a preferred embodiment, in which we consider an acoustic concentrator 22 and an acoustic balancer 24 to constitute a "pair" as shown for example in FIG. 3, there are at least two pairs of acoustic concentrators 22 and acoustic balancers 24 for each sensor element 30, 32. The at least one sensor element 30 (on the left side of the band 20) and the at least one sensor element 32 on the right side of band 20 may each comprise a piezoelectric material which in a preferred embodiment may be embedded inside band 20. One preferred conical shape of the acoustic concentrators 22 is shown in FIG. 3A. In FIG. 2A, the concentric circles depicting the bottom view of acoustic concentrators 22 show that the concentrators 22 are conical and may have a circular base.

If there are two sensors elements, then the sensors 30 may be connected in parallel electrically (the at least one sensor element 30 may comprise two physically separated sensors connected electrically). One can also define the two sensor elements 30 as one distributed sensor element. Positioning two sensors 30 on the two sides of the neck of the animal may provide a guaranteed contact with the body regardless of movement or position.

In one preferred embodiment used in the system or method of the present invention, annular band 20 may have at least two acoustic concentrators 22, projecting toward a neck or other portion of the pet animal from the working surface 20a at the one or more regions along the circumference of the band 20 that the at least one sensor element may be situated in. Likewise, collar 10 may have at least two acoustic balancers 24 projecting from the rear surface 20b at the one or more regions along the circumference of band 20 that the at least one sensor element may be situated in. As seen from FIG. 3, the at least two acoustic balancers 24 may be situated at a region along the circumference of the band 20 that is at least partly behind the at least two acoustic concentrators the at least one sensor 30, the at least two acoustic balancers situated opposite the at least two acoustic concentrators. Preferably, the at least two acoustic concentrators and the at least two acoustic balancers are situated so that one acoustic concentrator is directly opposite one corresponding acoustic balancer, as shown in FIG. 3. In some preferred embodiments, as shown in FIG. 3, the base end 23 of at least one acoustic balancer 24 is at least as wide as the base end 27 of the acoustic concentrator 22 that it is behind. More preferably, the one acoustic concentrator that is opposite its corresponding one acoustic balancer is of the same or similar shape as the corresponding one acoustic balancer. This may mean that a pair comprising one acoustic concentrator 22 and one acoustic balancer 24 at least partly behind it have the same overall shape, but in other preferred embodiments, it may mean that they have the same width, or that they have the same cross-section or the same shape at their base end 23 (the end facing the band 20) or the same width at their base end, or both have perpendicular diameters at their base ends or other structural similarities.

The acoustic concentrator 22 may touch the skin of the pet and absorb the noise from friction while conducting the signal and may penetrate the fur on the neck of the animal without causing the animal discomfort. This may be arranged by configuring the height of the projection (its length from the sensor element 30 substantially perpendicularly toward the neck of the pet animal) and thereby controlling how far the acoustic concentrator projects toward the direction of the neck of the pet animal. The comfort of the pet animal may be verified by testing the collar on various pet animals of the particular species.

In one preferred embodiment used in the system or method of the present invention, as shown in FIGS. 1-3A, collar 10 may include at least one sensor element 30 situated at one or more regions along a circumference of the band 20 and configured to measure at least one bioparameter relating to vital signs of the animal. The term "region" is not intended to indicate how much length the region has and the region can be as long as the band 20 or as narrow as a line, although as shown in FIG. 3 and FIG. 3A, it is preferably elongated along a circumference of the band 20. In a preferred embodiment, the at least one sensor element may be configured to measure at least one bioparameter from the following bioparameters: temperature, heart rate, respiration rate, movement. Preferably, the at least one sensor element is configured to measure at least two of the bioparameters, and more preferably at least three and most preferably all four of them.

The neck is a particularly suitable portion of the pet animal to monitor since it not only allows listening acoustically to two major blood vessels (arteries) but also monitoring a breathing pipe (the windpipe).

As shown in FIGS. 1-2A, band 20 may have a first side 21a and a second side 21b along its circumference. These "sides" may be portions of the circumference of band 20, for example on each side of a centrally located sensor element 33 (FIG. 3) (for example a temperature sensor 33a for measuring body temperature as shown in FIG. 2 and a temperature sensor 33b for measuring ambient temperature as shown in FIG. 1) and these "sides" should not be confused with the "vertically" opposite sides (working surface and rear surface) of or in relation to a sensor element 30 that the acoustic concentrators 22 and acoustic balancers 24 may be on. The first side 21a along the circumference of the band 20 may be on the left side of the neck of the animal and the second side 21b along the circumference of the band 20 may be the right side of the neck of the animal or vice versa. This may allow a most preferable embodiment in which at least one sensor element is positioned on the first side of the neck and at least one sensor element is positioned on the second side of the neck. FIG. 3 also shows a central portion 21c of the circumference of band 20 that may be located between sides 21a, 21b.

At least one sensor element 30 may be situated at one or more regions along a circumference of the band 20, and the at least one sensor element 30 may be configured to measure at least one bioparameter from the following bioparameters: temperature, heart rate, respiration rate, movement. As shown in FIG. 1, FIG. 3 and FIG. 3A, collar 10 may also include at least one acoustic concentrator 22 projecting as a bump toward the portion of the animal (for example the neck) from the working surface 20a. The at least one acoustic concentrator 22 may be situated at the one or more regions along the circumference and on a first vertical side (vertically speaking by reference to FIG. 3) of the at least one sensor element 30 that may be embedded in the band 20 (see FIG. 3). As also seen from FIGS. 2-3, at least one acoustic balancer 24 may be situated along the one or more regions of the circumference and may be projecting as a bump from the rear surface 20b of the band 20 on a second vertical side of the at least one sensor element. The position of the at least one acoustic balancer along the circumference of the band may be that it is at least partly behind, and preferably directly behind, the at least one acoustic concentrator 22.

As also shown in FIG. 3, a similar arrangement may exist on the other side 21b of the circumference of the band 20 with another at least one sensor 30 and another at least one acoustic concentrator 22 and another at least one acoustic balancer 24 similarly configured for example behind, and preferably directly behind, the at least one acoustic concentrator 22. This may allow monitoring both sides of the neck of the animal.

One or two or preferably all of the at least one acoustic concentrator 22 are wider at a concentrator base end 23 adjacent the working surface 20a than at a concentrator top end 25. For example, in FIG. 3A, the acoustic concentrators are conical. One or two or preferably all of the at least one acoustic balancers 24 are wider at a balancer base end 27 adjacent the rear surface 20b than at a balancer top end 29. In one preferred embodiment shown in FIGS. 4A-6B, the at least one acoustic concentrator 22 and the at least one acoustic balancer 24 are substantially circular in at least one dimension. An acoustic concentrator 22 of the at least one acoustic concentrator may be substantially semispherical. An acoustic balancer of the least one acoustic balancer may be substantially semispherical and may be located at least partly behind, and preferably directly behind, the acoustic balancer of the at least one acoustic concentrator on the first side 21a that is substantially semispherical. In other embodiments, the least one acoustic concentrator may be substantially semi-cylindrical (not shown) and the at least one acoustic balancer may be substantially semi-cylindrical (not shown) and located at least partly behind and preferably directly behind the one of the at least one acoustic concentrators that is substantially semispherical.

The acoustic concentrators 22 may be designed to optimize the acoustic transmission of sound vibrations from the pet animal's neck to the sensor element 30 in the band 20. In order to accomplish their purpose, the acoustic concentrators 22 and acoustic balancers 24 of the collar 10 may vary in terms of their size and in terms of their shape. With regard to their shape, an important aspect of their shape is the configuration of the base end of the acoustic concentrator or balancer. The base end of the acoustic concentrator (concentrator base end) and the base end of the acoustic balancer (balancer base end) arc each be closer to the sensor element 30 than the respective top ends (concentrator top end and balancer top end).

As shown in FIGS. 3, 3A, 4A, 5A, 6A, one or two or preferably all of the at least two acoustic concentrators 22 may be wider at a concentrator base end 23 adjacent the working surface 20a than at a concentrator top end 25. Likewise, as shown in FIGS. 3, 7A, 8A, 9A, one or preferably each of the at least two acoustic balancers 24 may be wider at a balancer base end 27 adjacent the rear surface 20b than at a balancer top end 29. The term "projecting" refers to the fact that the acoustic concentrators 22 and balancers 24 may project beyond the surface of the band 20, which may be relatively flat other than the acoustic concentrators and balancers. Although, these projections have been referred to as "bumps", the term "bump" is not intended as a limitation on the shape of the projections, although in many preferred embodiments, the "bumps" look like curved protrusions akin to a bump. In certain preferred embodiments, the acoustic concentrators 22 and acoustic balancers 24 are rounded and symmetrical.

Preferably, there are at least four sensor elements 30. Each sensor element 30 may be a strip of two inches to six inches in length depending on the size of the collar 10. In a preferred embodiment, there are at least two acoustic concentrators for each sensor element. For example, in one preferred embodiment where the sensor element is two and three-quarters inches, there may be four acoustic concentrators for that sensor 30. Acoustic concentrators 22 and acoustic balancers 24 may be located at the opposite sides of the sensor, as shown in FIG. 1 and FIG. 3. The collar 10 contains two sensors located symmetrically at the left and right sides of the neck.

The acoustic concentrators and the acoustic balancers may be integrally formed with the band and may be made of the same material as the band. For example, the bumps (acoustic concentrators and acoustic balancers) may be formed at the same time that the band is formed. Preferably, each of the at least two acoustic concentrators 22 are shaped like a bump, for example like a bump that diminishes in diameter from the concentrator base end to the concentrator top end. Likewise, preferably, each of the acoustic balancers are shaped like a bump, for example like a bump that diminishes in diameter from the balancer base end to the balancer top end. The bumps, in a preferred embodiment, may be mostly hollow except for particular structural elements in particular shapes that may fill the void of the hollow.

The acoustic concentrators 22 (or one particular acoustic concentrator of the at least one acoustic concentrator) and the acoustic balancers 24 (or one particular acoustic balancer of the at least one acoustic balancer) may be mathematically elliptical, for example substantially circular, in at least one dimension. Preferably, they may be substantially circular in two dimensions. As shown in FIGS. 2, 3, 4B, 5B, 6B, at least one, and preferably at least two, of the acoustic concentrators are substantially semispherical. Preferably, the shape of an acoustic balancer 24 mirrors the shape of the acoustic concentrators 22 that the balancer 24 faces on the opposite side of the band 20. Accordingly, preferably, at least one, and preferably at least two, of the at least two acoustic balancers 24 are substantially semispherical. In a different preferred embodiment (not shown), at least one of the at least two acoustic concentrators 22 is substantially semi-cylindrical and at least one of the at least two acoustic balancers 24 may also be substantially semi-cylindrical in this embodiment.

As shown in FIG. 6A-6B, each concentrator base end of the at least one or the at least two acoustic concentrators 22 may comprise a central dot 23b connected to the concentrator top end 25 along a linear axis 28. As shown in FIGS. 9A-9B, each balancer base end 27 of the at least one or the at least two acoustic balancers 24 may comprise a central dot 23b connected to a balancer top end 29 along a linear axle 28. In this embodiment, as shown in FIGS. 6A-6B and 9A-9B each acoustic concentrator 22 and each acoustic balancer 24 may be hollow except for the central dot and linear axle.

In one preferred embodiment of the concentrator base end 23 and the balancer base end 27, shown respectively in FIG. 4B and FIG. 7B, the X-shape 23a or perpendicular diameters may appear in a closed curve or a substantially closed curve. The "closed curve" may be a circular perimeter. As shown in FIG. 4B and FIG. 7B, the circular perimeter 23aa of the X-shape may be thicker than a thin outer perimeter and could in some preferred embodiments be thick enough to occupy 10% to 20% of the diameter/width of the concentrator base end 23 or of the balancer base end 29 (and in certain other preferred embodiments 5% to 10% or 15% to 30% or 3% to 6% or about 3% or about 5%, or about 10%, or about 15%, or about 20%, or about 25% or about 30% or other numbers depending on the embodiment of the diameter/width of the concentrator base end 23 or of the balancer base end 29). This proportion presupposes that the thickness of the perimeter is included in the calculation only once (not twice due to the two parts of the perimeter appearing 180 degrees apart from on another). As shown in FIG. 4A and FIG. 7A, the cross-section of the acoustic concentrators 22 and the acoustic balancers 24 may in the shape of an "X".

In certain other preferred embodiments, the acoustic concentrators and acoustic balancers are solid, as shown in FIG. 5B and FIG. 8B. In one preferred embodiment shown in FIGS. 2A and 3A, acoustic concentrators 22 are shaped like a cone.

Depending on the shape, the bumps comprising the acoustic concentrators and acoustic balancers may have a diameter of between 5 and 7 millimeters. Depending on the shape, the acoustic concentrators and acoustic balancers may also have a height of between 5 and 7 millimeters.

As a result of the acoustic concentrators and acoustic balancers in a preferred embodiment of the system 11 of the present invention, the signal to noise ratio expressed using the logarithmic decibel scale may be at least 20 dB and in some preferred embodiments between 20 dB and 40 dB. The typical pulse amplitude is between 300 and 500 mV, as defined by the gain setting of the amplifier (not shown).

In general, sensor elements 30 may be at least one sensor element 30 designed or configured to measure at least one bioparameter from among temperature, heart rate, respiration rate and movement. Alternatively, the sensor element may be for measuring a different vital sign. There could be more sensor elements and more bioparameters. For example, the at least one sensor element 30 may comprise at least two sensor elements 30 that may be configured or designed to measure at least two bioparameters from among temperature, heart rate, respiration and movement. Alternatively, the at least two sensor elements 30 may be for measuring at least two bioparameters from among temperature, heart rate, respiration rate and movement (or alternatively other vital signs). One sensor element may measure multiple bioparameters, for example, in the case of an acoustic sensor that measures respiration rate and heart rate. The at least two sensor elements may comprise four or more sensor elements designed to measure four or more bioparameters or specifically those four: temperature, heart rate, respiration rate and movement. In some preferred embodiments, the array of sensor elements 30 are designed to measure one or two bioparameters (in other preferred embodiments three or four) from the following bioparameters: temperature, heart rate, respiration rate, movement (for example horizontal and vertical movement) and positions.

The sensor elements 30 may be designed or configured to measure at least two different vital sign bioparameters as well as to measure certain bioparameters, such as movement, that may be useful in understanding a pet's vital signs when combined with other vital sign bioparameters. Each of the various sensor elements 30 on the band 20 may be designed for measuring a different vital sign parameter or in some cases there may be more than one sensor element measuring a particular vital sign bioparameter or more than one vital sign measured by a particular sensor element 30.

A sensor array (see FIG. 11) may include an acoustic sensor element 30e (piezoelectric element) for measuring pulse (heart rate) and an acoustic sensor for measuring respiration rate. Such a sensor array may include an accelerometer 30a to measure movement and vibrations of air traveling through the pet's air canals during inhaling and exhaling motions as well as the movement of blood traveling through the main blood vessels across the pet's neck. As shown in FIG. 11, the sensor array may also include a surface temperature/skin temperature sensor 30b to measure the surface temperature of the pet's body and an ambient temperature sensor 30f to measure the ambient temperature.

A sensor array may also include a microphone 30c. A sensor array may further include a microphone to listen to special noises made by a pet animal, for example a dog. In the case of a dog, there are about twenty-six separate sounds that they normally make. These include the following: barking sounds (including guarding/warning bark, alarm barking, playing, anxiety, need bark), yelping, growling, howling, eating, drinking, breathing (including normal breathing through the nose (inspiration and expiration), open-mouthed breathing, dry cough, wet cough, stertor, stridor, laryngeal paralysis, wheezing, rales/crackles, bronchio-vesicular sounds), vomiting/retching, regurgitation, grunting, groaning, and panting. In the case of a cat, the cat may additionally make hissing, meowing or purring sounds. Furthermore, each of these types of sounds may be further subdivided into sounds of those type made by a small dog, made by a large dog, made by a deep-chested dog and made by a puppy dog or a cat. Accordingly, the sounds picked up by a microphone may be interpreted by one ore more local processors 40 having an associated memory storage 67 (FIG. 11) of collar 10 or by one or more remote processors 40A of a remote computer terminal 69 (FIG. 12) and/or by a processor, such as at a server 70, having access to a dedicated or remote database to determine the type of sound and its interdependence with other vital sign bioparameters in order to arrive at a tentative diagnosis, to determine whether an alert is justified or to suggest treatment.

The sensor array 30 may also include a gyroscope 30*d* for capturing the vertical and/or horizontal movement of the pet. In the case of dogs, there are numerous basic dog postures that provide information as to what the dog is doing and thereby assist in interpreting vital sign measurements to arrive at a tentative diagnosis. The following basic dog postures that may be detected by sensor elements 30, for example a gyroscope, an accelerometer and/or a magnetometer: lying down laterally or right or left sides, lying down sternally (head up/down), lying on back, sitting, standing on four legs, standing on back legs, jumping, trotting, running, eating/drinking, urinating (male/female), defecating, limping hind leg, limping front leg, scratching hind leg, shaking leg, turning to lick, and stretching. The processor 40 make receive this information from the sensors 30 and utilize it in reaching a conclusion that it transmits remotely to the appropriate destination.

Each of the sensors 30 may be activated, de-activated, fine-tuned, set for predetermined repeated intervals or otherwise calibrated or controlled remotely, and in some embodiments also manually by a person located at the collar 10. "Remotely" means remote from the collar 10 and may include by a person in a vital sign monitoring station or a remotely stationed veterinarian or a medical center or the pet owner or the authorities or any other suitable location.

Collar 10 may further include a remotely-actuatable speaker (not shown) for communicating sounds to the pet animal remotely and may include a remotely actuatable light (such as an LED or other light source) for illuminating the pet animal to those seeking to locate it. The speaker and light may also be actuatable manually in person. The speaker and light may be situated on or attached to the band 20 and may be included in a sensor array (even though the light is not a sensor).

As seen from FIG. 3, collar 10 may also include a controller 49 that includes a local processor 40 that may be affixed to the collar 10 for example in a housing (not shown) attached to the collar 10. As shown in FIG. 3, local processor 40 may also include a processing unit having MicroElectro Mechanical Systems ("MEMS") technology. As also shown from FIG. 3, local processor 40 may be hard-wired or otherwise in electronic communication with each of the sensor elements 30. One or more local or remote processors may be configured to receive a signal representing data sensed by one or more of the sensor elements 30 and may be configured to analyze the data and communicate vital sign determinations and other data to a telecommunications system. The vital sign data measured by the sensor elements 30 of collar 10 may be relayed to and interpreted by processor 40 or by a remote processor (not shown). One or more local processors 40 or remote processors 40A may execute algorithms to interpret a collection of the physiological data sensed by the sensor elements and the interdependence of the vital sign data from the sensor elements and may arrive at a tentative diagnosis. The vital sign data may also include physiological data such as data about the movement of the pet animal (or other physiological data such as the saltiness of the animal's skin) since this physiological data, when combined with fundamental vital signs such as breathing rate, respiration rate, pulse, temperature, etc. may be useful in diagnosis by the veterinarian or remote computer server for the automatic temporary diagnosis by the processor 40.

Controller 49 may also include a memory storage 67 for storing health information history of the pet animal, the memory storage accessible by the processor 40. The memory storage can be a flash memory or other memory storage devices known in the art.

As shown in FIG. 11, collar 10 may include a communication device 68 such as a wireless transmitter unit, that may be accompanied by a receiving unit 68*a* forming a two-way communication device for communication to a remote station which may include a computer server pre-programmed to interact with the processor 40 or the remote station may communication with or include a veterinarian who can remotely measure vital signs using the collar's processor to select particular sensor elements to be activated to measure vital signs of the pet. As shown in FIG. 12, there is an option for there to be a remote station 70 (which may be a remote computer server having a remote processor 40A) which may also alert a pet owner or the authorities by sending an email communication 90*a* (FIG. 12) or an SMS alert 90*b* (FIG. 12). The communication device may also incorporate short range or long range wireless communication technology such as UHF, Wi-Fi, Bluetooth, etc. and cellular technology.

The collar 10 and/or server computer or other part of the system such as the one or more local or remote processors may issue an alert based on predefined parameters (e.g. unique prior knowledge regarding the specific animal) and/or behavioral (e.g. erratic or uncharacteristic movements) or vital signs parameters. The specific measurements of the animal (height, length, weight etc.) and relevant history, as well of the population of animals of that species or breed or type, may be loaded into the device and/or the system during a registration procedure. The unique identification data of the animal can also include: the pet animal's name, owner's names, personal details (address, phone number etc.), medical information concerning the pet and any other relevant data. The information may be included in the processing by the one or more local or remote processors 40, 40A when the one or more local or remote processors 40, 40A analyze data from the sensor elements 30.

A GPS device may be incorporated into collar 10. The GPS device could take the form, for example, of an integrated circuit or an RFID. Other location awareness technology may also be incorporated into the collar 10.

The receiving unit 68 attached to or incorporated into the collar 10 may be a smart phone, mobile (and/or hand-held) device, or any other communication/messaging device, or a specifically designed receiver or reader. The receiving unit 68 may be connected to the collar 10 in a wired and/or wireless manner as mentioned above. The receiving unit 68 may be detachable from the collar 10 for direct connection to a computer terminal, in order to enable faster or more secure downloading of stored (and in some cases processed) sensor data.

The collar 10 and/or system may gather analytical information including statistics, trend analysis, comparative analysis etc. regarding particular pets, particular breeds of pets or particular species of animals. The system may incorporate a social network for other animal owners for the purpose of sharing information.

The following are non-limiting examples of vital sign and/or other physiological data for dogs acquired from sensor elements 30. In general, dog sounds recorded by a microphone may be combined with information from other sensor elements 30 regarding dog postures and dog movements and this may be further combined with information from other sensor elements 30 such as temperature, respiration rate and pulse and other available data such as the time of day, the ambient temperature, the pet's normal behavior, the context etc. The processor 40 may reach conclusions about the presence of a high probability of medical conditions suffered by dogs or cats or other pet animals, such as hypothermia, hyperthermia, slow heart rate, normal sinus arrhythmia or abnormal arrhythmia, ear infections, torn ligaments, gastric dilatation, dyspnea, gastritis, pruritus and osteoarthritis. For example, hypothermia occurs when heat loss/output exceeds heat production. It can happen in cold weather, especially to small or sick animals, or under sedation or anesthesia. If low body temperature is recorded by the sensor elements 30 at a time when the ambient temperature is very cold, an alert may be sent. In another case, if a slower than normal heart rate is detected by sensor elements 30 in a pet animal the movements of the pet animal may be checked to determine if an alert needs to be sent. In general, the pulse rate may be compared to the respiration rate over time to see if the heart rate increases when the animal takes a breath. Regarding ear infections in a dog, if the sensor 30 input indicates movements consistent with an ear infections and the microphone sensor indicates sounds of pain when the ears are touched, an alert may be sent. Inflammation of the bones and joints is a common disease of older dogs. If the sensor input indicates decreased or change in activity relative to the time of day and sounds of pain, an alert may be transmitted.

A method may also include, in some embodiments, a step of transmitting vital sign measurements to the pet owner, a veterinarian, a remote computer server or the authorities when the vital sign measurement exceeds a threshold level. Accordingly, processor 40 may be programmed to compare data received from the sensor elements to threshold levels of respiration rate, heart rate, temperature, movement, blood pressure, and/or other physiological data, such as noises made by a dog. Furthermore, the processor may have access to software in controller 49 that utilizes a function or a formula to relate combinations of the sensor element data. For example, if a dog moves in a certain way and utters a certain noise, that may trigger a particular alert or diagnosis. In addition, the programmer 40 may have access to its own data comparing the physiological data of a particular vital sign or combination of vital signs to the average vital sign data for pets of that species, that breed and that geographical location, taking into consideration the ambient temperature and the medical history of the pet. The controller/processor may transmit an alert to the pet owner, to a veterinarian or to the authorities.

A processor 40 affixed to the collar 10 may be in electronic communication with each of the at least two, or at least three or at least four sensor elements. The processor 40 may control a timing of an "ON" status of each sensor sufficient to trigger taking of a vital sign measurement. Memory storage 67 (FIG. 3) may be flash memory or other well known types of memory storage accessible by processor 40. The memory storage unit 67 may store data regarding the power requirements of each of the sensor elements in sensor array 30 as well as the lifespan of the battery 61 or other power source in collar 10. Alternatively, this data may be accessible by the processor 40 since processor 40 may be in communication with remote databases. As a result, the processor 40 may be configured to calculate the timing of the "ON" status of a sensor element (or of two or more or all the sensor elements) based on power requirements of the at least four sensors and a lifespan of the power source. In addition, processor 40 may receive sensor data from the sensor elements and communicate vital sign status of the pet animal to a remote location. The processor 40 may reach overall conclusions as to whether the pet has a particular medical condition by accessing databases and utilizing software containing diagnostic algorithms.

As seen from FIG. 13, the present invention may be a method 200 of monitoring pet animals to determine a suspicion of a specific medical condition in the pet animals. Method 200 may comprise a step 210 of providing an annular band on the pet animal to wrap around a portion of the pet animal and to have at least two sensor elements situated at one or more regions along a circumference of the band, the at least two sensor elements including an accelerometer and a non-accelerometer sensor, the accelerometer configured to measure at least one accelerometer-measured bioparameter of the pet animal from among: resting patterns, activity patterns, movement patterns, position patterns (such as relating to the pet animal relieving itself), lameness and scratching, and the non-accelerometer sensor configured to measure at least one of the following non-accelerometer-measured bioparameters of the pet animal: temperature, pulse rate, respiration rate.

Method 200 may also include a step 220 of one or more local or remote processors receiving (a) sensor output data from the sensor array concerning the measured bioparameters and (b) reference data concerning the measured bioparameters of the pet animal or of a population of the pet animal, the one or more remote or local processors configured to determine whether a specific medical condition is suspected by at least one of the following:

(i) scoring at least two bioparameters relative to the reference data and comparing a cumulative score of all scored bioparameters to a threshold cumulative score or to a threshold cumulative range; or (ii) identifying an abnormal pattern in at least one bioparameter from among the accelerometer-measured bioparameters and the non-accelerometer-measured bioparameters. Method 200 may include a step 300 of the one or more remote or local processors sending an alert if at least one specific medical condition is suspected.

In some versions of method 200, there may be a step of configuring the annular band with at least one acoustic concentrator and at least one acoustic balancer so as to reduce signal to noise ratio. There may also be a step of configuring each of the at least one acoustic concentrator to be conical in shape. In some versions of method 200, there may be a step of requiring the sensor output data from the sensor array concerning the bioparameters to pass a quality assurance test, the quality assurance test being based on a threshold level of signal to noise ratio.

Particular features described in the context of one embodiment may be able to be incorporated into other embodiments for which that feature was not specifically mentioned.

This patent application hereby incorporates by reference in its entirety Applicant's previously filed U.S. Patent Application having Publication No. 20130014706 published Jan. 17, 2013 having the Title "Pet Animal Collar for Health and Vital Signs Monitoring, Alert & Diagnosis" and having a filing date of Feb. 21, 2012 and Applicant's previously filed U.S. patent application Ser. No. 13/743,383 having the Title "Acoustically Enhanced Pet Animal Collar for Health & Vital Signs Monitoring, Alert and Diagnosis" filed Jan. 17, 2013, that is yet to be published.

The following lists certain examples of data sensed by an accelerometer, and certain examples of data sensed by an accelerometer combined data sensed by other sensors, which may be utilized in certain preferred embodiments of the present invention.

For Accelerometer Only
  Resting Patterns in an Adult Dog
    Description—dogs spend approximately 70% of their time lying down, mostly on the side (lateral recumbency), sometimes on their sternum (ventral recumbency) and rarely on their back (dorsal recumbency). It is unknown exactly how much time is spent resting in an average dog. It is likely that this figure varies greatly between different individuals and influenced by various factors, such as age, size, breed, presence of other people/animals, health condition and lifestyle.
    Normal range—determined by the system individually for each animal, which requires a short learning period.
    Mostly motionless, except for short breaks of minimal movements for changing posture, location, looking around briefly, etc.
    Includes breakdown of time spent in each: left or right lateral, dorsal or ventral recumbency.
    Includes breakdown per hour of day and day of the week (to "learn" the dog's individual routine and lifestyle).
  Sensory input—
  Accelerometer—
  Resting in any one posture with occasional switching.
  Relatively short breaks of activity or exercise.
  Alerts—
  Detect trends of small changes over relatively long periods of time in overall time spent resting.
  Detect significant changes over relatively short periods of time in overall time spent resting.
  Detect trends of small changes over relatively long periods of time in overall time spent in each posture.
  Detect significant changes over relatively short periods of time in overall time spent in each posture.
  Detect changes over time in specific properties of each posture.
  Activity Patterns in an Adult Dog
    Description—dogs exercise habits vary dramatically based on age, size, breed, presence of other people/animals, health condition and lifestyle. Most dogs don't spend much time engaging in physical activities.
    Normal range—determined by the system individually for each animal, which requires a short learning period.
    Different types of activity patterns for each dog—walking, jogging, wrestling, fetching, etc.
    Includes breakdown per hour of day and day of the week (to "learn" the dog's individual routine and lifestyle).
  Sensory input—
  Accelerometer—exercise, activity, lack of resting. The data is complementing the resting use case.
  Alerts—
  Detect persistent changes in specific properties of each activity.
  Urination—Male and Female Adult Dog
    Description—normally, dogs urinate only when let outside (for in-house dogs). Some dogs void completely in one try (common in females) and some void multiple times during a walk to mark a territory and communicate with other dogs (common in males). Most dogs urinate only few times a day and can abstain for many hours. Most dogs don't urinate at night. Individual variability exists.
    Normal range—determined by the system individually for each animal, which requires a short learning period.
    Breakdown to number of attempts per day and time spent in each attempt.
    Breakdown per hour of day and day of week.
    Distinguish crouching and leg-lifting postures
  Sensory input—
  Accelerometer—
    Assuming urination posture
    Log number of times
    Log time spent in each try
    Log time interval between subsequent urinations (e.g. a male dog on a walk may urinate several times in close succession).
  Note—normal (voluntary voiding) urination always takes place during walking or standing activity.
  Alerts—
  Detect trends of small changes over relatively long periods of time in overall time spent urinating.
  Detect trends of small changes over relatively long periods of time in overall urination attempts.
  Detect significant changes over relatively short periods of time in overall urination attempts.
  Detect persistent changes in properties of postural tendencies.
  Lameness
    Description—abnormal gait is always an indication of pathology. It may result from a problem in one or more legs, vertebral column or nervous system.
    Normal range—regular pattern of movements and regular level of activity as determined for this individual, which will require a short learning period.
  Sensory input—
  Accelerometer—
    Alterations in patterns of movement—lying down, sitting, walking and running
    Decreased overall level of activity
    Commonly, the problem starts during, or right after, exercise.
    Alterations may appear only during enhanced activity
    Alterations may appear after prolonged rest and get better with activity (or "warming up").
  Alerts—Detect persistent movement abnormalities
  Scratching
    Description—scratching can take place at any part of the body using all 4 legs or the mouth. Excessive scratching, termed pruritus, is abnormal and may be acute or chronic, focal or generalized. There is no established normal amount for scratching activity. It is assumed that a normal adult dog scratches up to 10 times a day at different places and mostly during the day. Scratching is mostly done while lying down or sitting and rarely while standing. It shouldn't normally last for more than a few seconds.

Normal range—determined by the system individually for each animal, which requires a short learning period.

Breakdown to number of episodes per day and time spent in each episode.

Breakdown per hour of day and day of week.

Sensory input—

Accelerometer—turning and scratching with hind legs, fore legs, or mouth.
  Breakdown to type of scratching
  Analyze—focal or generalized pruritus (scratching in more than one posture).

Alerts

Detect trends of small changes over relatively long periods of time in overall time spent scratching.

Detect significant changes over relatively short periods of time in overall number of scratching episodes.

Detect significant changes over relatively short periods of time in overall scratching episodes and time spent scratching.

For Accelerometer Combined With Other Sensors

Seizure/Convulsions

Description—involuntary muscle contractions and twitching. May result from various systemic diseases, nervous system disorders, or epilepsy. Grand Mal seizure is associated with loss of consciousness, lying down, foaming, paddling with the legs, and sometimes vocalizing. Petit Mal, or partial seizure, may involve just a brief episode of abnormal behavior or twitching without loss of consciousness.

Normal range—no seizure activity.

Sensory input—

Accelerometer—
  Detect movement pattern associated with seizures (necessary and sufficient component)
  Count number of seizures and the length of each episodes
  Document activity pattern 30 minutes before and after a seizure Sound—whining, yelping (supporting component)

Pulse—increased pulse rate or irregular rhythm (strong supporting component)

Respiration—increased respiratory rate or irregular rhythm (supporting component)

Alert—create an alert for any seizure episode, regardless of type or duration.

Gastric Dilatation-Volvulus (GDV)

Description—GDV is an emergency, life-threatening condition, in which the stomach rotates and twists on itself. As a result the stomach entry and exit points get blocked and it starts to fill with gas. Successful management and outcome depends on early detection and prompt diagnosis.

Normal range—normal behavior and parameters. The following attributes may increase the risk for developing GDV and thereby indicate enhanced monitoring.

Large breed, deep-chested dogs are at higher risk (GSH, Doberman, Poodles, Great Dane, St. Bernards, Irish Setters, Gordon Setters).

Incidence increases with age, most common at age 7-10.

Dogs previously undergoing splenectomy.

Dogs exercising after consuming a large meal.

Sensory input—

Accelerometer—
  Restlessness, reluctance to lie down, pacing (supporting component).
  GDV often develops at evening/night; so increased aforementioned activity at times when dog usually is resting may serve as further indication (strong supporting component).
  Increased respiratory effort when lying down (supporting component).

Sounds—
  Vomiting, retching (supporting component).
  Not eating (supporting component).
  Grunting/groaning (supporting component).
  Pain (supporting component).

Respiration—increased rate and effort (supporting component).

Pulse rate—
  Increased pulse rate (supporting component).
  Rhythm may become irregular (supporting component).
  Loss of sinus arrhythmia (supporting component).

Typical pattern—ingestion of a large meal (sound) followed by exercise (accelerometer, pulse, respiration) and repeated attempts to vomit (sound, accelerometer)—strong supporting component.

Alert—create an alert for any such episode.

Hyperthyroidism

Description—the most common hormonal disease in cats, affecting approximately 10% of the older cat population.

Normal range—normal parameters.

Sensory input—

Basic data (the following attributes may increase the risk for developing hyperthyroidism and thereby indicate enhanced monitoring)—
  Age—over 10
  Breed—Siamese and Himalayan are at decreased risk.
  Diet—eating solely canned food, preference for seafood or fish flavored canned food increase the risk.
  Environment—living mostly indoors, sleeping on floors, using litter-boxes, increase the risk (possibly through exposure to PBDE's).

Accelerometer—
  Increased activity level
  Some show weakness
  Ventroflexion (bowed-down head)

Sound—
  Increased appetite.
  Some cases may have anorexia.
  Increased frequency of drinking
  Increased time spent drinking
  Vomiting
  Diarrhea Pulse rate—increased rate, possibly irregular rhythm.

Respiration—increased rate.

Proximity sensors—
  Increased number of visits to the litter box
  Increased frequency and time spent drinking and eating.

Alert—create an alert for any such combination or partial combination of signs.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A method of monitoring a pet animal to determine a suspicion of a specific medical condition in the pet animal, the pet animal being a dog or a cat, the method comprising:
   providing a collar, the collar having an annular band, the band having a working surface configured to wrap around a neck of the pet animal, the collar also configured to have at least two sensor elements situated along a circumference of the band, the at least two sensor elements including an accelerometer and a non-accelerometer sensor, the accelerometer configured to measure at least one accelerometer-measured bioparameter of the pet animal from among: resting patterns, activity patterns, movement patterns, position patterns, lameness and scratching, and the non-accelerometer sensor configured to measure the following non-accelerometer-measured bioparameters of the pet animal: (a) temperature and (b) at least one of (i) pulse rate and (ii) respiration rate, wherein the at least one of pulse rate and respiration rate is measured by at least one acoustic sensor;
   providing the band with at least one acoustic balancer projecting from a rear surface of the band at one or more regions along the circumference of the band and with at least one acoustic concentrator along the circumference of the band, the at least one acoustic concentrator integrally formed with the band, projecting radially inward from the working surface and having a dimension along an axis that projects radially inward from the working surface, the at least one acoustic concentrator configured in shape to penetrate a fur of the neck of the pet animal and reduce relative movement between the collar and the pet animal when a head of the pet animal moves so as to, together with the at least one acoustic balancer, reduce noise, capture a low frequency sound, conduct a readable signal from the neck to the at least one acoustic sensor, and improve accuracy of position outputs by the accelerometer;
   receiving, by one or more local or remote processors, (a) sensor output data from the sensor array concerning the measured bioparameters and (b) reference data concerning the measured bioparameters of the pet animal or of a population of the pet animal, the one or more remote or local processors configured to determine whether a specific medical condition is suspected by at least one of the following:
   (i) scoring at least two bioparameters relative to the reference data and comparing a cumulative score of all scored bioparameters to a threshold cumulative score or to a threshold cumulative range; or
   (ii) identifying an abnormal pattern in at least one bioparameter from among the accelerometer-measured bioparameters and the non-accelerometer-measured bioparameters;
   performing, by the one or more remote or local processors, a quality assurance test on said sensor input data for the at least one accelerometer-measured bioparameter and applying results of said quality assurance test to said sensor output data that is considered a necessary component for detecting the at least one specific medical condition such that: (i) if said sensor output data passes the quality assurance test said sensor output data is deemed a sufficient condition for detecting the at least one specified medical condition and the one or more remote or local processors are configured to send an alert, whereas (ii) if said sensor output data fails the quality assurance test, sensor output data from the non-accelerometer-measured bioparameters of the pet animal is processed,
   wherein the monitoring by the collar of the vital signs is such that the signal to noise ratio is sufficiently high, and outputs of the accelerometer are sufficiently accurate, for the monitoring of the vital signs to be sufficiently accurate to assist in diagnosing the health condition of the pet animal.

2. The method of claim 1, further comprising requiring the sensor output data from the sensor array concerning the bioparameters to pass the quality assurance test based on a threshold level of signal to noise ratio.

3. The method of claim 1, further comprising configuring each of the at least one acoustic concentrator to be substantially conical in shape.

4. The method of claim 1, further comprising configuring the at least one acoustic concentrator to comprise two acoustic concentrators of substantially equal length, along the axis that projects radially inward from the working surface.

5. The method of claim 1, further comprising combining the identifying of the abnormal pattern in the at least one bioparameter with identifying abnormal patterns in at least one other bioparameter.

6. The method of claim 1, wherein the identifying of the abnormal pattern in the at least one bioparameter involves identifying said abnormal patterns in at least one accelerometer-measured bioparameter and identifying abnormal patterns in at least one non-accelerometer-measured bioparameter.

7. The method of claim 1, further comprising the one or more remote or local processors sending an alert if at least one specific medical condition is suspected.

8. The method of claim 7, wherein the specific medical condition is seizure and the abnormal pattern in the at least one accelerometer-measured bioparameters is an abnormal pattern of movement comprising at least one of paddling, head shaking or twitching occurring when the pet animal is lying down on either side, the abnormal pattern of movement sensed by the accelerometer.

9. The method of claim 8, wherein the one or more remote or local processors are configured to determine a suspicion of seizure based also on at least one of sound, pulse and respiration, wherein pulse means pulse rate or pulse rhythm.

10. The method of claim 7, wherein the specific medical condition is gastric dilation-volvulus (GDV) and the one or more remote or, local processors are configured to base a suspicion of GDV at least in part on
   scoring at least two bioparameters from among (i) restlessness including reluctance to lie down or pacing, (ii) vomiting sounds (iii) sounds indicative of not eating, (iv) sounds indicative of grunting or groaning, (v) sounds indicative of pain, (vi) increased respiration rate and respiration effort, (vii) increased pulse rate (viii) irregular pulse rhythm (ix) loss of sinus arrhythmia, and (x) a pattern of ingestion of a large meal followed by exercise followed by attempts to vomit,
   and comparing a cumulative score of all scored bioparameters to a threshold cumulative score or to a threshold cumulative range.

11. The method of claim 7, wherein the specific medical condition is hyperthyroidism and the one or more remote or local processors, are configured to
   base a suspicion of hyperthyroidism at least in part on
   scoring at least two bioparameters from among (i) increased activity level, vomiting sounds (iii) sounds indicative of not eating, (iv) sounds indicative of vomiting or diarrhea, (v) increased pulse rate or irregular pulse rate, (vi) increased respiration rate, (vii) increased number of visits to a litter box (viii) increased frequency or e spent of drinking as measured by acoustic accelerometer, (ix) increased frequency and time spent eating as measured by proximity sensors, comparing a cumulative score of all scored bioparameters to a threshold cumulative score or to a threshold cumulative range; and measuring a persistence over time of either the cumulative score or the abnormal pattern.

12. The method of claim 1, wherein the sensor array is configured to measure at least one of the following characteristics of the pet animal for output to the one or more remote or local processors; sleeping/resting patterns, eating/drinking patterns, position patterns relating to the amoral relieving itself and existence of stress or pain.

13. The method of claim 1, further comprising communicating, using a two-way communication device, the detected at least one specified medical condition in a form of an alert to a remotely stationed veterinarian or other user.

14. The method of claim 1, wherein the one or more remote or local processors are configured to determine whether a new parameter, that is a function of a combination of each of the at least two bioparameters, exceeds a threshold level or range.

15. The method of claim 1, wherein the annular band comprises a layer of an elastic material.

16. The method of claim 1, wherein the at least one acoustic balancer is situated at the one or more regions along the circumference at least partly behind the at least one acoustic concentrator.

17. The method of claim 1, further comprising
each of the at least one acoustic concentrator wider at a concentrator base end adjacent the working surface than at a concentrator top end,
the at least one acoustic balancer wider at a balancer base end adjacent the rear surface than at a balancer top end.

18. The method of claim 1, wherein the quality assurance test is based on a pattern recognition.

19. The method of claim 1, wherein the quality assurance test is based on whether a quantity of data points is sufficient.

20. The method of claim 1, wherein the accelerometer is an acoustic accelerometer configured to measure sounds, and wherein the sounds comprise measuring a presence of at least four pet animals sounds among yelping, whining, wheezing, hissing, purring, stridor, stertor, couphing, barking, growling and grunting.

* * * * *